(12) United States Patent
Dyell et al.

(10) Patent No.: US 12,396,667 B2
(45) Date of Patent: Aug. 26, 2025

(54) ALARM FATIGUE MANAGEMENT SYSTEMS AND METHODS

(71) Applicant: VCCB Holdings, Inc., Wilmington, DE (US)

(72) Inventors: David Dyell, Panama City, FL (US); Christopher Rogowski, Newtown Square, PA (US); Scott Kahler, Tuscaloosa, AL (US); Jennifer Milan, Westminster, CO (US)

(73) Assignee: VCCB Holdings, Inc., Wilmington, DE (US)

( * ) Notice: Subject to any disclaimer, the term of this patent is extended or adjusted under 35 U.S.C. 154(b) by 0 days.

(21) Appl. No.: 18/323,187

(22) Filed: May 24, 2023

(65) Prior Publication Data

US 2023/0363678 A1    Nov. 16, 2023

Related U.S. Application Data

(63) Continuation of application No. 17/028,822, filed on Sep. 22, 2020, now Pat. No. 11,696,712, which is a
(Continued)

(51) Int. Cl.
| | |
|---|---|
| *A61B 5/00* | (2006.01) |
| *A61B 5/16* | (2006.01) |
| *G16H 40/63* | (2018.01) |

(52) U.S. Cl.
CPC ............ *A61B 5/162* (2013.01); *A61B 5/746* (2013.01); *G16H 40/63* (2018.01)

(58) Field of Classification Search
CPC ......... A61B 5/162; A61B 5/746; G16H 40/63
See application file for complete search history.

(56) References Cited

U.S. PATENT DOCUMENTS

| | | | |
|---|---|---|---|
| 4,960,128 A | 10/1990 | Gordon et al. | |
| 4,964,408 A | 10/1990 | Hink et al. | |
| (Continued) | | | |

FOREIGN PATENT DOCUMENTS

| | | |
|---|---|---|
| WO | WO 98/038909 | 9/1998 |
| WO | WO 02/051354 | 7/2002 |
| (Continued) | | |

OTHER PUBLICATIONS

US 2022/0192529 A1, 06/2022, Al-Ali et al. (withdrawn)
(Continued)

*Primary Examiner* — Nay Tun
(74) *Attorney, Agent, or Firm* — Knobbe, Martens, Olson & Bear, LLP

(57) ABSTRACT

An apparatus for modifying alarms at a medical device for alarm fatigue management is provided and includes an alarm monitor, an alarm filter, an alarm modifier, a memory element for storing data, and a processor that executes instructions associated with the data, wherein the processor and the memory element cooperate such that the apparatus is configured for receiving an alarm condition from an alarm management engine, the alarm condition based on an alarm fatigue level of a user of the medical device, the alarm fatigue level based on at least a user fatigue model, a medical device model and a patient condition, receiving an alarm from the medical device, modifying the alarm according to the alarm condition, the alarm condition being configured to increase a likelihood of the user responding to the modified alarm, and generating an alarm indicator based on the modification.

20 Claims, 7 Drawing Sheets

Related U.S. Application Data continuation of application No. 16/735,476, filed on Jan. 6, 2020, now Pat. No. 10,813,580, which is a continuation of application No. 16/155,006, filed on Oct. 9, 2018, now Pat. No. 10,524,712, which is a continuation of application No. 14/738,658, filed on Jun. 12, 2015, now Pat. No. 10,123,729.

(60) Provisional application No. 62/011,643, filed on Jun. 13, 2014.

(56) References Cited

U.S. PATENT DOCUMENTS

| | | |
|---|---|---|
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,494,043 A | 2/1996 | O'Sullivan et al. |
| 5,533,511 A | 7/1996 | Kaspari et al. |
| 5,561,275 A | 10/1996 | Savage et al. |
| 5,590,649 A | 1/1997 | Caro et al. |
| 5,602,924 A | 2/1997 | Durand et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,890,929 A | 4/1999 | Mills et al. |
| 5,919,134 A | 7/1999 | Diab |
| 5,987,343 A | 11/1999 | Kinast |
| 5,997,343 A | 12/1999 | Mills et al. |
| 6,002,952 A | 12/1999 | Diab et al. |
| 6,010,937 A | 1/2000 | Karam et al. |
| 6,027,452 A | 2/2000 | Flaherty et al. |
| 6,040,578 A | 3/2000 | Malin et al. |
| 6,066,204 A | 5/2000 | Haven |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,152,754 A | 11/2000 | Gerhardt et al. |
| 6,184,521 B1 | 2/2001 | Coffin, IV et al. |
| 6,232,609 B1 | 5/2001 | Snyder et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,280,381 B1 | 8/2001 | Malin et al. |
| 6,285,896 B1 | 9/2001 | Tobler et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,334,065 B1 | 12/2001 | Al-Ali et al. |
| 6,360,114 B1 | 3/2002 | Diab et al. |
| 6,368,283 B1 | 4/2002 | Xu et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,505,059 B1 | 1/2003 | Kollias et al. |
| 6,525,386 B1 | 2/2003 | Mills et al. |
| 6,526,300 B1 | 2/2003 | Kiani et al. |
| 6,534,012 B1 | 3/2003 | Hazen et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,585,645 B2 | 7/2003 | Hutchinson |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,606,511 B1 | 8/2003 | Ali et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,658,276 B2 | 12/2003 | Kiani et al. |
| 6,661,161 B1 | 12/2003 | Lanzo et al. |
| 6,681,003 B2 | 1/2004 | Linder et al. |
| 6,697,656 B1 | 2/2004 | Al-Ali |
| 6,697,658 B2 | 2/2004 | Al-Ali |
| RE38,476 E | 3/2004 | Diab et al. |
| RE38,492 E | 4/2004 | Diab et al. |
| 6,738,652 B2 | 5/2004 | Mattu et al. |
| 6,738,671 B2 | 5/2004 | Christophersom et al. |
| 6,760,607 B2 | 7/2004 | Al-Ali |
| 6,788,965 B2 | 9/2004 | Ruchti et al. |
| 6,816,241 B2 | 11/2004 | Grubisic |
| 6,822,564 B2 | 11/2004 | Al-Ali |
| 6,850,787 B2 | 2/2005 | Weber et al. |
| 6,850,788 B2 | 2/2005 | Al-Ali |
| 6,876,931 B2 | 4/2005 | Lorenz et al. |
| 6,882,883 B2 | 4/2005 | Condie et al. |
| 6,920,345 B2 | 7/2005 | Al-Ali et al. |
| 6,934,570 B2 | 8/2005 | Kiani et al. |
| 6,943,348 B1 | 9/2005 | Coffin IV |
| 6,956,649 B2 | 10/2005 | Acosta et al. |
| 6,957,107 B2 | 10/2005 | Rogers et al. |
| 6,961,598 B2 | 11/2005 | Diab |
| 6,970,792 B1 | 11/2005 | Diab |
| 6,985,764 B2 | 1/2006 | Mason et al. |
| 6,990,364 B2 | 1/2006 | Ruchti et al. |
| 6,998,247 B2 | 2/2006 | Monfre et al. |
| 7,003,338 B2 | 2/2006 | Weber et al. |
| 7,015,451 B2 | 3/2006 | Dalke et al. |
| 7,027,849 B2 | 4/2006 | Al-Ali |
| 7,027,872 B2 | 4/2006 | Thompson |
| 7,077,806 B2 | 7/2006 | Ackermann et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,133,710 B2 | 11/2006 | Acosta et al. |
| 7,142,901 B2 | 11/2006 | Kiani et al. |
| 7,156,809 B2 | 1/2007 | Quy |
| 7,181,283 B2 | 2/2007 | Hettrick et al. |
| 7,225,006 B2 | 5/2007 | Al-Ali et al. |
| RE39,672 E | 6/2007 | Shehada et al. |
| 7,229,409 B2 | 6/2007 | Ito et al. |
| 7,248,916 B2 | 7/2007 | Bardy |
| 7,254,429 B2 | 8/2007 | Schurman et al. |
| 7,254,431 B2 | 8/2007 | Al-Ali et al. |
| 7,254,434 B2 | 8/2007 | Schulz et al. |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,356,365 B2 | 4/2008 | Schurman |
| 7,371,981 B2 | 5/2008 | Abdul-Hafiz |
| 7,373,193 B2 | 5/2008 | Al-Ali et al. |

(56) References Cited

U.S. PATENT DOCUMENTS

| | | |
|---|---|---|
| 7,377,794 B2 | 5/2008 | Al-Ali et al. |
| 7,395,158 B2 | 7/2008 | Monfre et al. |
| 7,415,297 B2 | 8/2008 | Al-Ali et al. |
| 7,438,683 B2 | 10/2008 | Al-Ali et al. |
| 7,483,729 B2 | 1/2009 | Al-Ali et al. |
| D587,657 S | 3/2009 | Al-Ali et al. |
| 7,500,950 B2 | 3/2009 | Al-Ali et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| D592,507 S | 5/2009 | Wachman et al. |
| 7,530,942 B1 | 5/2009 | Diab |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,715,919 B2 | 5/2010 | Osorio et al. |
| 7,729,733 B2 | 6/2010 | Al-Ali et al. |
| 7,761,127 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,612 B2 | 9/2010 | Johnson et al. |
| RE41,912 E | 11/2010 | Parker |
| 7,880,626 B2 | 2/2011 | Al-Ali et al. |
| 7,909,772 B2 | 3/2011 | Popov et al. |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,941,199 B2 | 5/2011 | Kiani |
| 7,957,780 B2 | 6/2011 | Lamego et al. |
| 7,962,188 B2 | 6/2011 | Kiani et al. |
| 7,967,749 B2 | 6/2011 | Hutchinson et al. |
| 7,976,472 B2 | 7/2011 | Kiani |
| 7,990,382 B2 | 8/2011 | Kiani |
| 8,002,701 B2 | 8/2011 | John et al. |
| 8,008,088 B2 | 8/2011 | Bellott et al. |
| RE42,753 E | 9/2011 | Kiani-Azarbayjany et al. |
| 8,028,701 B2 | 10/2011 | Al-Ali et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,123,720 B2 | 2/2012 | Solomon |
| 8,126,735 B2 | 2/2012 | Dicks et al. |
| 8,130,105 B2 | 3/2012 | Al-Ali et al. |
| 8,165,893 B1 | 4/2012 | Goldberg et al. |
| 8,182,443 B1 | 5/2012 | Kiani |
| 8,183,451 B1 | 5/2012 | Panaiotis |
| 8,190,223 B2 | 5/2012 | Al-Ali et al. |
| 8,203,438 B2 | 6/2012 | Kiani et al. |
| 8,203,704 B2 | 6/2012 | Merritt et al. |
| 8,219,172 B2 | 7/2012 | Schurman et al. |
| 8,224,411 B2 | 7/2012 | Al-Ali et al. |
| 8,229,532 B2 | 7/2012 | Davis |
| 8,233,955 B2 | 7/2012 | Al-Ali et al. |
| 8,255,026 B1 | 8/2012 | Al-Ali |
| 8,255,240 B2 | 8/2012 | O'Hanlon et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,310,374 B2 | 11/2012 | Grubis et al. |
| 8,315,683 B2 | 11/2012 | Al-Ali et al. |
| RE43,860 E | 12/2012 | Parker |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,374,665 B2 | 2/2013 | Lamego |
| 8,388,353 B2 | 3/2013 | Kiani et al. |
| 8,395,498 B2 | 3/2013 | Gaskill et al. |
| 8,401,602 B2 | 3/2013 | Kiani |
| 8,414,499 B2 | 4/2013 | Al-Ali et al. |
| 8,417,662 B2 | 4/2013 | Gawlick |
| 8,418,524 B2 | 4/2013 | Al-Ali |
| 8,425,414 B2 | 4/2013 | Eveland |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,438,038 B2 | 5/2013 | Cosentino et al. |
| 8,451,113 B2 | 5/2013 | Mazar et al. |
| 8,455,290 B2 | 6/2013 | Siskavich |
| 8,457,707 B2 | 6/2013 | Kiani |
| 8,471,713 B2 | 6/2013 | Poeze et al. |
| 8,473,020 B2 | 6/2013 | Kiani et al. |
| 8,487,758 B2 | 7/2013 | Istoc |
| 8,509,867 B2 | 8/2013 | Workman et al. |
| 8,515,509 B2 | 8/2013 | Bruinsma et al. |
| 8,523,781 B2 | 9/2013 | Al-Ali |
| D692,145 S | 10/2013 | Al-Ali et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,584,345 B2 | 11/2013 | Al-Ali et al. |
| 8,588,880 B2 | 11/2013 | Abdul-Hafiz et al. |
| 8,630,691 B2 | 1/2014 | Lamego et al. |
| 8,641,631 B2 | 2/2014 | Sierra et al. |
| 8,652,060 B2 | 2/2014 | Al-Ali |
| 8,666,468 B1 | 3/2014 | Al-Ali |
| 8,670,811 B2 | 3/2014 | O'Reilly |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,702,627 B2 | 4/2014 | Telfort et al. |
| 8,712,494 B1 | 4/2014 | MacNeish, III et al. |
| 8,715,206 B2 | 5/2014 | Telfort et al. |
| 8,718,949 B2 | 5/2014 | Blomquist et al. |
| 8,723,677 B1 | 5/2014 | Kiani |
| 8,740,792 B1 | 6/2014 | Kiani et al. |
| 8,755,535 B2 | 6/2014 | Telfort et al. |
| 8,755,872 B1 | 6/2014 | Marinow |
| 8,764,671 B2 | 7/2014 | Kiani |
| 8,768,423 B2 | 7/2014 | Shakespeare et al. |
| 8,771,204 B2 | 7/2014 | Telfort et al. |
| 8,781,544 B2 | 7/2014 | Al-Ali et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,840,549 B2 | 9/2014 | Al-Ali et al. |
| 8,852,094 B2 | 10/2014 | Al-Ali et al. |
| 8,852,994 B2 | 10/2014 | Wojtczuk et al. |
| 8,897,847 B2 | 11/2014 | Al-Ali |
| 8,911,377 B2 | 12/2014 | Al-Ali |
| 8,989,831 B2 | 3/2015 | Al-Ali et al. |
| 8,998,809 B2 | 4/2015 | Kiani |
| 9,066,666 B2 | 6/2015 | Kiani |
| 9,066,680 B1 | 6/2015 | Al-Ali et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,131,881 B2 | 9/2015 | Diab et al. |
| 9,138,180 B1 | 9/2015 | Coverston et al. |
| 9,153,112 B1 | 10/2015 | Kiani et al. |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,095 B1 | 12/2015 | Al-Ali |
| 9,218,454 B2 | 12/2015 | Kiani et al. |
| 9,245,668 B1 | 1/2016 | Vo et al. |
| 9,267,572 B2 | 2/2016 | Barker et al. |

(56) References Cited

U.S. PATENT DOCUMENTS

| | | |
|---|---|---|
| 9,277,880 B2 | 3/2016 | Poeze et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,392,945 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,474,474 B2 | 10/2016 | Lamego et al. |
| 9,480,435 B2 | 11/2016 | Olsen |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,560,996 B2 | 2/2017 | Kiani |
| 9,579,039 B2 | 2/2017 | Jansen et al. |
| 9,582,988 B2 | 2/2017 | Gross |
| 9,622,692 B2 | 4/2017 | Lamego et al. |
| D788,312 S | 5/2017 | Al-Ali et al. |
| 9,649,054 B2 | 5/2017 | Lamego et al. |
| 9,697,928 B2 | 7/2017 | Al-Ali et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,749,232 B2 | 8/2017 | Sampath et al. |
| 9,750,442 B2 | 9/2017 | Olsen |
| 9,750,461 B1 | 9/2017 | Telfort |
| 9,775,545 B2 | 10/2017 | Al-Ali et al. |
| 9,778,079 B1 | 10/2017 | Al-Ali et al. |
| 9,782,077 B2 | 10/2017 | Lamego et al. |
| 9,787,568 B2 | 10/2017 | Lamego et al. |
| 9,808,188 B1 | 11/2017 | Perea et al. |
| 9,839,379 B2 | 12/2017 | Al-Ali et al. |
| 9,839,381 B1 | 12/2017 | Weber et al. |
| 9,847,749 B2 | 12/2017 | Kiani et al. |
| 9,848,800 B1 | 12/2017 | Lee et al. |
| 9,861,298 B2 | 1/2018 | Eckerbom et al. |
| 9,861,305 B1 | 1/2018 | Weber et al. |
| 9,877,650 B2 | 1/2018 | Muhsin et al. |
| 9,891,079 B2 | 2/2018 | Dalvi |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,055,974 B2 | 8/2018 | Wilson |
| 10,086,138 B1 | 10/2018 | Novak, Jr. |
| 10,111,591 B2 | 10/2018 | Dyell et al. |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,813,580 B2 | 10/2020 | Dyell et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |

(56) References Cited

U.S. PATENT DOCUMENTS

| | | |
|---|---|---|
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| D989,327 S | 6/2023 | Al-Ali et al. |
| 11,678,829 B2 | 6/2023 | Al-Ali et al. |
| 11,679,579 B2 | 6/2023 | Al-Ali |
| 11,684,296 B2 | 6/2023 | Vo et al. |
| 11,692,934 B2 | 7/2023 | Normand et al. |
| 11,696,712 B2 | 7/2023 | Dyell et al. |
| 11,701,043 B2 | 7/2023 | Al-Ali et al. |
| D997,365 S | 8/2023 | Hwang |
| 11,721,105 B2 | 8/2023 | Ranasinghe et al. |
| 11,730,379 B2 | 8/2023 | Ahmed et al. |
| D998,625 S | 9/2023 | Indorf et al. |
| D998,630 S | 9/2023 | Indorf et al. |
| D998,631 S | 9/2023 | Indorf et al. |
| D999,244 S | 9/2023 | Indorf et al. |
| D999,245 S | 9/2023 | Indorf et al. |
| D999,246 S | 9/2023 | Indorf et al. |
| 11,766,198 B2 | 9/2023 | Pauley et al. |
| D1,000,975 S | 10/2023 | Al-Ali et al. |
| 11,803,623 B2 | 10/2023 | Kiani et al. |
| 11,832,940 B2 | 12/2023 | Diab et al. |
| D1,013,179 S | 1/2024 | Al-Ali et al. |
| 11,872,156 B2 | 1/2024 | Telfort et al. |
| 11,879,960 B2 | 1/2024 | Ranasinghe et al. |
| 11,883,129 B2 | 1/2024 | Olsen |
| D1,022,729 S | 4/2024 | Forrest et al. |
| 11,951,186 B2 | 4/2024 | Krishnamani et al. |
| 11,974,833 B2 | 5/2024 | Forrest et al. |
| 11,986,067 B2 | 5/2024 | Al-Ali et al. |
| 11,986,289 B2 | 5/2024 | Dalvi et al. |
| 11,986,305 B2 | 5/2024 | Al-Ali et al. |
| D1,031,729 S | 6/2024 | Forrest et al. |
| 12,004,869 B2 | 6/2024 | Kiani et al. |
| 12,014,328 B2 | 6/2024 | Wachman et al. |
| D1,036,293 S | 7/2024 | Al-Ali |
| D1,037,462 S | 7/2024 | Al-Ali et al. |
| 12,029,844 B2 | 7/2024 | Pauley et al. |
| 12,048,534 B2 | 7/2024 | Vo et al. |
| 12,064,217 B2 | 8/2024 | Ahmed et al. |
| 12,066,426 B1 | 8/2024 | Lapotko et al. |
| D1,041,511 S | 9/2024 | Indorf et al. |
| D1,042,596 S | 9/2024 | DeJong et al. |
| D1,042,852 S | 9/2024 | Hwang |
| 12,076,159 B2 | 9/2024 | Belur Nagaraj et al. |
| 12,082,926 B2 | 9/2024 | Sharma et al. |
| D1,044,828 S | 10/2024 | Chandran et al. |
| D1,048,571 S | 10/2024 | Yu et al. |
| D1,048,908 S | 10/2024 | Al-Ali et al. |
| 12,106,752 B2 | 10/2024 | Campbell et al. |
| 12,114,974 B2 | 10/2024 | Al-Ali et al. |
| 12,126,683 B2 | 10/2024 | Koo et al. |
| 12,127,838 B2 | 10/2024 | Olsen et al. |
| 12,128,213 B2 | 10/2024 | Kiani et al. |
| 12,131,661 B2 | 10/2024 | Pauley et al. |
| D1,050,910 S | 11/2024 | Al-Ali et al. |
| 12,178,572 B1 | 12/2024 | Pauley et al. |
| 12,178,581 B2 | 12/2024 | Telfort et al. |
| 12,178,852 B2 | 12/2024 | Kiani et al. |
| D1,057,159 S | 1/2025 | DeJong et al. |
| D1,057,160 S | 1/2025 | DeJong et al. |
| 12,198,790 B1 | 1/2025 | Al-Ali |
| 12,200,421 B2 | 1/2025 | Campbell et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0103001 A1 | 5/2004 | Mazar et al. |
| 2004/0106163 A1 | 6/2004 | Workman, Jr. et al. |
| 2005/0055242 A1 | 3/2005 | Bello et al. |
| 2005/0055276 A1 | 3/2005 | Kiani et al. |
| 2005/0101841 A9 | 5/2005 | Kaylor et al. |
| 2005/0234317 A1 | 10/2005 | Kiani |
| 2006/0064020 A1 | 3/2006 | Burnes et al. |
| 2006/0073719 A1 | 4/2006 | Kiani |
| 2006/0074722 A1 | 4/2006 | Chu |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2008/0027499 A1 | 1/2008 | Srivathsa et al. |
| 2008/0064965 A1 | 3/2008 | Jay et al. |
| 2008/0094228 A1 | 4/2008 | Welch et al. |
| 2008/0103375 A1 | 5/2008 | Kiani |
| 2008/0146895 A1* | 6/2008 | Olson ............... G16H 40/67 600/301 |
| 2008/0221418 A1 | 9/2008 | Al-Ali et al. |
| 2009/0036759 A1 | 2/2009 | Ault et al. |
| 2009/0048500 A1* | 2/2009 | Corn ............... A61B 5/4094 600/315 |
| 2009/0076342 A1 | 3/2009 | Amurthur et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275807 A1 | 11/2009 | Sitzman et al. |
| 2009/0275813 A1 | 11/2009 | Davis |
| 2009/0275844 A1 | 11/2009 | Al-Ali |
| 2009/0299162 A1 | 12/2009 | Brauker et al. |
| 2010/0004518 A1 | 1/2010 | Vo et al. |
| 2010/0030040 A1 | 2/2010 | Poeze et al. |
| 2010/0070188 A1 | 3/2010 | Solomon |
| 2010/0099964 A1 | 4/2010 | O'Reilly et al. |
| 2010/0234718 A1 | 9/2010 | Sampath et al. |
| 2010/0259395 A1 | 10/2010 | Nuthi |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0077967 A1 | 3/2011 | Kapu et al. |
| 2011/0082711 A1 | 4/2011 | Poeze et al. |
| 2011/0087081 A1 | 4/2011 | Kiani et al. |
| 2011/0118561 A1 | 5/2011 | Tari et al. |
| 2011/0137297 A1 | 6/2011 | Kiani et al. |
| 2011/0172498 A1 | 7/2011 | Olsen et al. |
| 2011/0172743 A1 | 7/2011 | Davis et al. |
| 2011/0183650 A1* | 7/2011 | McKee ............... H04M 1/724 455/567 |
| 2011/0230733 A1 | 9/2011 | Al-Ali |
| 2012/0123231 A1 | 5/2012 | O'Reilly |
| 2012/0165629 A1 | 6/2012 | Merritt et al. |

(56) References Cited

U.S. PATENT DOCUMENTS

| | | |
|---|---|---|
| 2012/0209084 A1 | 8/2012 | Olsen et al. |
| 2012/0215559 A1* | 8/2012 | Flanagan ............. G16H 15/00 705/3 |
| 2012/0226117 A1 | 9/2012 | Lamego et al. |
| 2012/0238854 A1 | 9/2012 | Blomquist et al. |
| 2012/0277543 A1 | 11/2012 | Homchowdhury et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0162424 A1 | 6/2013 | Treacy |
| 2013/0237770 A1 | 9/2013 | Sullivan et al. |
| 2013/0267791 A1 | 10/2013 | Halperin et al. |
| 2013/0296672 A1 | 11/2013 | O'Neil et al. |
| 2013/0345921 A1 | 12/2013 | Al-Ali et al. |
| 2014/0142963 A1* | 5/2014 | Hill ...................... G16H 10/60 705/2 |
| 2014/0166076 A1 | 6/2014 | Kiani et al. |
| 2014/0180160 A1 | 6/2014 | Brown et al. |
| 2014/0187973 A1 | 7/2014 | Brown et al. |
| 2014/0275871 A1 | 9/2014 | Lamego et al. |
| 2014/0275872 A1 | 9/2014 | Merritt et al. |
| 2014/0316217 A1 | 10/2014 | Purdon et al. |
| 2014/0316218 A1 | 10/2014 | Purdon et al. |
| 2014/0323897 A1 | 10/2014 | Brown et al. |
| 2014/0323898 A1 | 10/2014 | Purdon et al. |
| 2015/0005600 A1 | 1/2015 | Blank et al. |
| 2015/0011907 A1 | 1/2015 | Purdon et al. |
| 2015/0073241 A1 | 3/2015 | Lamego |
| 2015/0080754 A1 | 3/2015 | Purdon et al. |
| 2015/0099950 A1 | 4/2015 | Al-Ali et al. |
| 2015/0106121 A1 | 4/2015 | Muhsin et al. |
| 2015/0186608 A1 | 7/2015 | Fuller et al. |
| 2015/0257654 A1 | 9/2015 | Bennett-Guerrero |
| 2015/0310733 A1 | 10/2015 | Gross |
| 2016/0196388 A1 | 7/2016 | Lamego |
| 2016/0367173 A1 | 12/2016 | Dalvi et al. |
| 2017/0024748 A1 | 1/2017 | Haider |
| 2017/0042488 A1 | 2/2017 | Muhsin |
| 2017/0055896 A1 | 3/2017 | Al-Ali |
| 2017/0173632 A1 | 6/2017 | Al-Ali |
| 2017/0251974 A1 | 9/2017 | Shreim et al. |
| 2017/0311891 A1 | 11/2017 | Kiani et al. |
| 2018/0103874 A1 | 4/2018 | Lee et al. |
| 2018/0199871 A1 | 7/2018 | Pauley et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0021930 A1 | 1/2020 | Iswanto et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Ai-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |
| 2023/0210417 A1 | 7/2023 | Al-Ali et al. |
| 2023/0222805 A1 | 7/2023 | Muhsin et al. |
| 2023/0222887 A1 | 7/2023 | Muhsin et al. |
| 2023/0226331 A1 | 7/2023 | Kiani et al. |
| 2023/0284916 A1 | 9/2023 | Telfort |
| 2023/0284943 A1 | 9/2023 | Scruggs et al. |
| 2023/0301562 A1 | 9/2023 | Scruggs et al. |
| 2023/0346993 A1 | 11/2023 | Kiani et al. |
| 2023/0368221 A1 | 11/2023 | Haider |
| 2023/0371893 A1 | 11/2023 | Al-Ali et al. |
| 2023/0389837 A1 | 12/2023 | Krishnamani et al. |
| 2024/0016418 A1 | 1/2024 | Devadoss et al. |
| 2024/0016419 A1 | 1/2024 | Devadoss et al. |
| 2024/0047061 A1 | 2/2024 | Al-Ali et al. |
| 2024/0049310 A1 | 2/2024 | Al-Ali et al. |
| 2024/0049986 A1 | 2/2024 | Al-Ali et al. |
| 2024/0081656 A1 | 3/2024 | DeJong et al. |
| 2024/0122486 A1 | 4/2024 | Kiani |
| 2024/0180456 A1 | 6/2024 | Al-Ali |
| 2024/0188872 A1 | 6/2024 | Al-Ali et al. |
| 2024/0245855 A1 | 7/2024 | Vo et al. |
| 2024/0260894 A1 | 8/2024 | Olsen |

(56) References Cited

U.S. PATENT DOCUMENTS

| | | |
|---|---|---|
| 2024/0267698 A1 | 8/2024 | Telfort et al. |
| 2024/0277233 A1 | 8/2024 | Al-Ali |
| 2024/0277280 A1 | 8/2024 | Al-Ali |
| 2024/0298920 A1 | 9/2024 | Fernkbist et al. |
| 2024/0306985 A1 | 9/2024 | Vo et al. |
| 2024/0324953 A1 | 10/2024 | Telfort |
| 2024/0380246 A1 | 11/2024 | Moran |
| 2024/0380247 A1 | 11/2024 | Moran |
| 2025/0000458 A1 | 1/2025 | Abdul-Hafiz et al. |

FOREIGN PATENT DOCUMENTS

| | | |
|---|---|---|
| WO | WO 03/094090 | 11/2003 |
| WO | WO 2008/116295 | 10/2008 |
| WO | WO 2013/056180 | 4/2013 |
| WO | WO 2013/076481 | 5/2013 |

OTHER PUBLICATIONS

US 2024/0016391 A1, 01/2024, Lapotko et al. (withdrawn)
Cvach, Maria, "Monitor Alarm Fatigue: An Integrative Review", Biomedical Instrumentation & Technology, July/Aug. 2012, pp. 268-277.
Lorincz et al., "Sensor Networks for Emergency Response: Challenges and Opportunities", Pervasive Computing, Oct.-Dec. 2004, pp. 16-23.
Lukowicz et al., "Amon: A Wearable Medical Computer for High Risk Patients", Proceedings of the 6th International Symposium on Wearable Computers (ISWC'02), pp. 2.

\* cited by examiner

ALARM FATIGUE MANAGEMENT SYSTEMS AND METHODS

CROSS-REFERENCE TO RELATED APPLICATION

This application is a continuation of U.S. patent application Ser. No. 17/028,822, filed on Sep. 22, 2020, which is a continuation of U.S. patent application Ser. No. 16/735,476, filed on Jan. 6, 2020, now issued as U.S. Pat. No. 10,813,580 on Oct. 27, 2020, entitled ALARM FATIGUE MANAGEMENT SYSTEMS AND METHODS, which is a continuation of U.S. patent application Ser. No. 16/155,006, filed on Oct. 9, 2018, now issued as U.S. Pat. No. 10,524,712 on Jan. 7, 2020, and entitled ALARM FATIGUE MANAGEMENT SYSTEMS AND METHODS, which is a continuation of U.S. patent application Ser. No. 14/738,658, filed on Jun. 12, 2015, now issued as U.S. Pat. No. 10,123,729 on Nov. 13, 2018, and entitled ALARM FATIGUE MANAGEMENT SYSTEMS AND METHODS which relates to and claims the benefit of priority under 35 U.S.C. § 119(e) to U.S. Provisional Patent Application Ser. No. 62/011,643, filed on Jun. 13, 2014 and entitled ALARM FATIGUE MANAGEMENT SYSTEMS AND METHODS, the disclosures of each of which are hereby incorporated by reference in their entirety.

TECHNICAL FIELD

This disclosure relates in general to the field of healthcare systems and, more particularly, to systems and methods related to alarm fatigue management.

BACKGROUND

The background description includes information that may be useful in understanding the present disclosure. It is not an admission that any of the information provided herein is prior art or relevant to the disclosure, or that any publication specifically or implicitly referenced is prior art.

Alarm fatigue is desensitization to alarms brought on by overexposure to excessive alarms, which can result in reduced response times or even complete failure to respond to critical issues that are raised by the alarms in the first place. Alarm fatigue is increasingly a serious problem in a variety of different industries and professions. In particular, medical professionals can experience alarm fatigue so severe that alarms indicating life threatening conditions are at times overlooked, resulting in numerous deaths each year. Various systems tailored towards modifying delivery of alarms exist in the healthcare marketplace. One such system creates alert signals based on information or data from medical systems. The alert signals can take the form of music that is generated using the information or data from the medical system, creating a wide variety of signals that simultaneously pass information to an intended recipient. Another system reduces false alarms in a certain predetermined region around a medical device. A medical professional has a portable transmitter/monitor, and when an alert condition exists, the system will check the physical proximity of the transmitter/monitor. In the event the transmitter/monitor is within the predetermined region defined as a false alarm region, the alert is concealed.

In yet another example, portable alert devices deliver alerts to an intended recipient. The portable alert devices perform a scan to gather relevant information about the device's surroundings prior to issuing an alert. In doing so, they can alter the mode of an alert depending on the environment that the portable devices and the intended recipient are in. In yet another example device, when a user is supposed to pump insulin, the device provides an alarm. To reduce alarm fatigue, the device includes a randomization module that can generate random alarms. Randomness of alarms is determined by historical stability of the user's blood glucose level. Thus, a user with a more stable blood glucose level will be rewarded with fewer alerts to check their blood glucose level. Another system creates "super-alarms."

BRIEF DESCRIPTION OF THE DRAWINGS

To provide a more complete understanding of the present disclosure and features and advantages thereof, reference is made to the following description, taken in conjunction with the accompanying figures, wherein like reference numerals represent like parts, in which.

DETAILED DESCRIPTION OF EXAMPLE EMBODIMENTS

Overview

An apparatus for modifying alarms at a medical device for alarm fatigue management is provided and includes an alarm monitor, an alarm filter, an alarm modifier, a memory element for storing data, and a processor that executes instructions associated with the data, wherein the processor and the memory element cooperate such that the apparatus is configured for receiving an alarm condition from an alarm management engine, the alarm condition based on an alarm fatigue level of a user of the medical device, the alarm fatigue level based on at least a user fatigue model, a medical device model and a patient condition, receiving an alarm from the medical device, modifying the alarm according to the alarm condition, the alarm condition being configured to increase a likelihood of the user responding to the modified alarm, and generating an alarm indicator based on the modification.

EXAMPLE EMBODIMENTS

Figure 1:
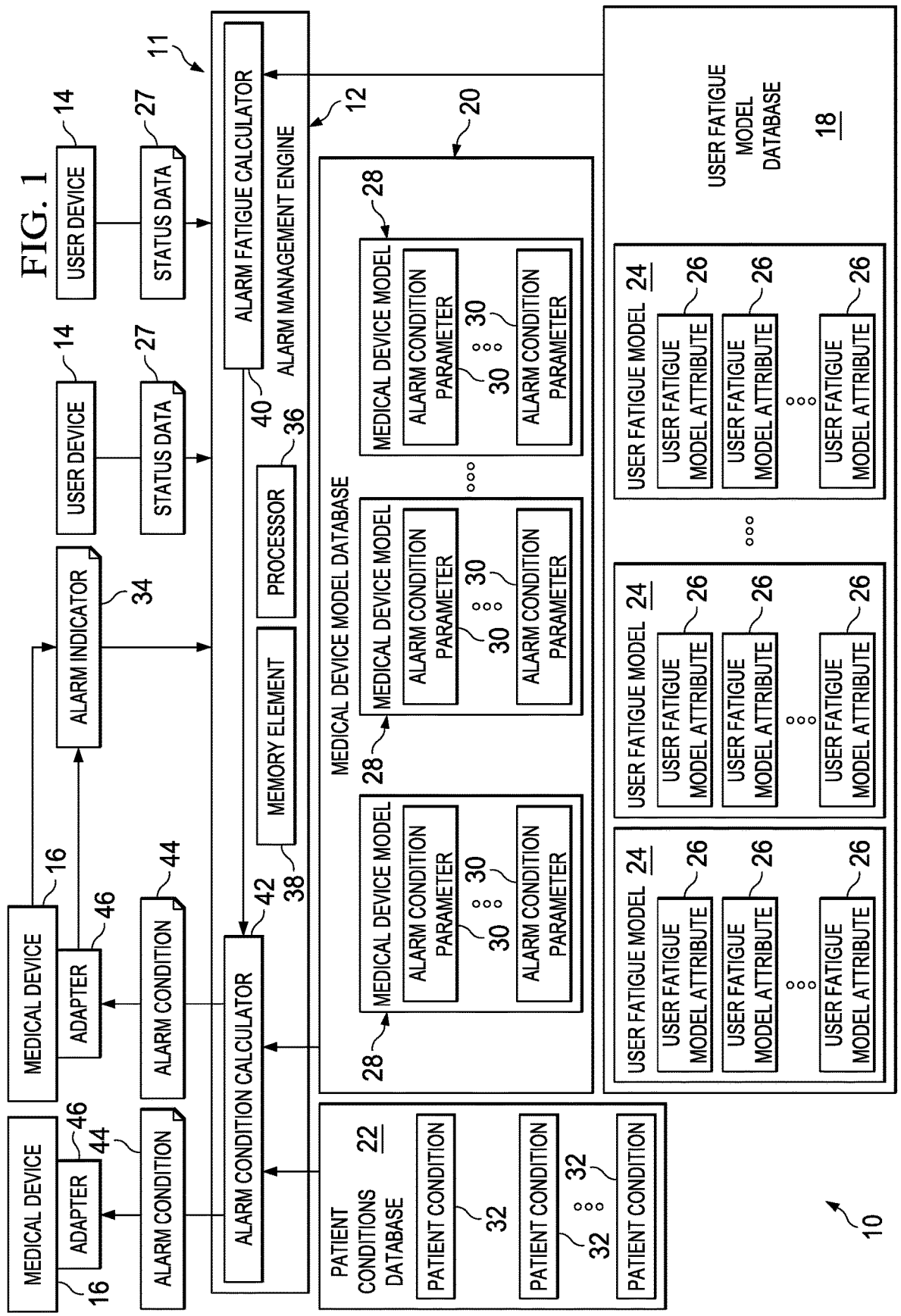
FIG. 1 is a simplified block diagram illustrating a system for alarm fatigue management according to an example embodiment.

Turning to FIG. 1, FIG. 1 is a simplified block diagram illustrating a system 10 according to an example embodiment. System 10 comprises a network 11 (generally indicated by an arrow) connecting an alarm management engine 12 with one or more user devices 14 and medical devices 16. Alarm management engine 12 interfaces with a user fatigue model database 18, a medical device model database 20, and a patient conditions database 22. User fatigue model database 18 can include a plurality of user fatigue model 24 corresponding to different users or stakeholders of system 10. Each user fatigue model 24 can include one or more user fatigue model attribute 26.

User fatigue model attribute 26 can comprise factors (e.g., characteristics) that can affect a user's fatigue level. User fatigue model attribute 26 can include many different types of information, including information conveyed via status data 27 from user device 14 and information entered into user fatigue model database 18 by other means, based on details about a particular user. In various embodiments, status data 27 can modify user fatigue model attribute 26 of user fatigue model 24. For example, user fatigue model attribute 26 comprises a number of hours worked by the user; status data 27 can indicate that the user worked for 8 hours. In another example, user fatigue model attribute 26 comprises a shift information for users on a particular floor of a hospital; status data 27 can indicate that the shift is a night shift.

In a general sense, status data 27 comprises data corresponding to various measurable quantities related to a particular user. Status data 27 can include physiological information (e.g., stress level (as measured by various measurable parameters such as blood pressure, heart rate, etc.), neurological activity, brain electrical activity, hormone levels, body temperature, breathing rate, blood sugar level, age, change of position, sleep activity (e.g., amount of sleep over previous 24 hours and time since last sleep), etc.), alarm response time information, user shift data (e.g., if user is not on active duty, user may ignore alarm), environmental alarm data (e.g., number of alarms received at user device), and various other parameters that can indicate a likelihood of the corresponding user responding to, or ignoring, an alarm signal. In some embodiments, status data 27 can be communicated with an associated timestamp corresponding to a time of data collection/measurement. In some embodiments, one or more correlations between a physiological reaction and an alarm signal may be discerned.

User shift data can include various details describing the user's shift, including the user's work schedule (e.g., weekly schedule, monthly schedule, yearly schedule, number of shifts worked without a day off, length of a shift, total time elapsed since the shift began, and/or number of shifts worked since the last vacation). For example, user shift data can indicate when a user works a late night shift followed by an early morning shift the next day. Status data 27 can also include an amount of user-directed alarms (e.g., the number of alarms the user has had to respond to), alarm response time data (e.g., the user's time to respond), alarm severity for at least one user-directed alarm, a number of repeated alarms (e.g., the number of alarms that have had to be repeated due to a delayed response or lack of a response), a number of missed alarms, a number of simultaneous alarms, a number of false alarms, etc.

Environment alarm data can include the number of alarms the user has been exposed to (e.g., both alarms directed to the user and alarms directed to other users), the loudness of an alarm the user has been exposed to, the frequency of alarms the user has been exposed to during a relevant time period (e.g., during a shift, during a day, during a week, during two weeks, during a month, during a year, since time of most recent vacation, and since time of most recent day off), and at least one alarm location (e.g., a location where the user heard an alarm).

In some embodiments, user fatigue model attribute 26 can be changed (e.g., updated) periodically or continuously, depending on the sampling frequency in an embodiment. Additionally, user fatigue model attribute 26 can contain historical data (e.g., longitudinal study data). Some examples of user fatigue model attribute 24 include personality factors and physiological factors. Personality factors are factors that might indicate a person is more or less prone to alarm fatigue (e.g., irritability, psychological disorders, and personality type). Physiological factors can include factors that pertain to a certain user's physical abilities (e.g., deafness, blindness, color blindness, sensitivity to particular light and/or sound patters, and varying degrees of disabilities related to these conditions and others).

Medical device model database 20 can include one or more medical device model 28. Medical device model 28 can comprise a data construct (e.g., an algorithmic model, a mathematical model, a digital model, an alphanumeric identifier, etc.) of medical device 16, a representation of an instrument reading (e.g., blood pressure measurement), or other suitable function. Note that the term "data construct" as used herein encompasses scalars, arrays, subarrays, matrices, vectors, and other data representations that are allocated in a region of memory in a memory element. The data constructs as used herein represent analog information (such as physical phenomena) with binary digits (or other computer interpretable representation) that are interpreted as integers, real numbers, characters, or other data types comprising a finite number of discrete symbols that represent essentially infinite variation of analog information. In other words, the data construct represents a physical entity in symbolic form, typically using symbols from a relatively small number of discrete enumerable symbols associated with a context and other properties of the physical entity being represented.

In some embodiments, medical device model 28 can comprise a data container for numerical values corresponding to device readings (e.g., measurements). Each medical device model 28 can include one or more alarm condition parameter 30. For example, one of medical device model 28 can comprise a model of a blood pressure monitor; alarm condition parameter 30 for such model may correspond to a blood pressure reading that indicates an alarm if the value of alarm condition parameter 30 exceeds a predetermined threshold or other criteria. In some embodiments, the threshold may be included in corresponding medical device model 28.

In another example, alarm condition parameter 30 comprises a threshold value for a physiological measurement of a patient measured by medical device 16. In yet another example, alarm condition parameter 30 comprises a maximum frequency at which medical device 16 generates an alarm. In yet another example, alarm condition parameter 30 comprises a frequency at which medical device 16 measures the patient. In yet another example, alarm condition parameter 30 comprises measurement sensitivity corresponding to medical device 16's ability to measure the patient. In various embodiments, each medical device 16 may be represented by corresponding medical device model 28 in medical device model database 20.

Patient conditions database 22 can include one or more patient condition 32. By way of examples, and not as limitations, patient condition 32 may include a data construct of an aggregate (e.g., collection, average, weighted average, composite, etc.) of health conditions, population characteristics (e.g., lack of dexterity or memory with older users; high mental workload for anesthesiologists in operating rooms; etc.), diseases, symptoms (e.g., subjective patient symptoms and observable symptoms such as temperature, analyte data, etc.), medications and various medical status. Examples of patient condition 32 include physical or mental health parameter values, such as blood glucose in diabetes, respiratory flow in asthma, blood pressure in hypertension, cholesterol in cardiovascular disease, weight in eating disorders, T-cell or viral count in HIV, and frequency or timing of episodes in mental health disorders.

In a general sense, patient condition 32 is indicative of a context of the physiological measurement by medical device 16 (e.g., context under which the alarms are generated at medical device 16). For example, alarms generated at medical device 16 may indicate a hypertension status of a patient when the alarms are directed towards, or result as a consequence of, high blood pressure of the patient. In another example, alarms generated at medical device 16 may indicate a serious condition of the patient when the alarms are directed towards, or result as a consequence of, various disparate physiological measurements of the patient.

In another example, patient condition 32 can refer to a medical status of the patient (e.g., "undetermined" may correspond to a status of a patient awaiting physician and assessment; "good" may indicate that vital signs (e.g., pulse rate, oxygen levels, blood pressure, etc.) are stable and within normal limits, with the patient being conscious and comfortable; "fair" may indicate that vital signs are stable and within normal limits with the patient being conscious, but uncomfortable; "serious" may indicate that vital signs are unstable and not within normal limits, with the patient being acutely ill; "critical" may indicate that vital signs are unstable and not within normal limits with the patient being unconscious; "deceased" may indicate that the patient is dead). In another example, patient condition 32 of "hypertension" may indicate that the patient suffers from hypertension, with expected high blood pressure readings; patient condition 32 of "diabetes" may indicate that the patient suffers from diabetes with higher than normal blood sugar readings without medication, etc. In some embodiments, patient condition 32 may correspond to a mathematical model (e.g., polynomial function, alphanumeric value, matrix, etc.) of a corresponding physical or mental health condition.

In some embodiments, alarm management engine 12 receives, in addition to user device status data 27, one or more alarm indicator 34 from one or more medical device 16. Alarm indicator 34 can indicate modifications to alarms generated at medical device 16, and can serve as feedback regarding the modifications (e.g., whether the modifications are effective). In some embodiments, alarm indicator 34 can also include signals (e.g., auditory, tactile, optical, vibratory, electrical, wireless, and/or other signals) that are indicative of, or associated with alarms configured on medical device 16. Alarm management engine 12 may include, in addition to a processor 36 and a memory element 38, an alarm fatigue calculator 40 and an alarm condition calculator 42. Alarm management engine 12 may be coupled to (and communicate with) adapter 46 associated with respective medical device 16.

During operation, alarm management engine 12 may receive status data 27 from user device 14. Status data 27 can be collected substantially continuously in some embodiments, and periodically (e.g., every 1, 5, 10, 15, 20, 30, 45 second and/or every 1, 5, 10, 15, 30, 45 minutes) in other embodiments. In some embodiments, status data 27 may be collected in predetermined time intervals or ranges (e.g., every 0-5 seconds, 5-10 seconds, 10-15 seconds, 15-20 seconds, 20-30 seconds, 30-45 seconds, 45-60 seconds and/or every 0-5, 5-10, 10-15, 15-30, or 30-45 minutes). Additionally, status data 27 may be collected on a "push" basis (e.g., in response to certain triggers such as alerts and responses to alerts) with user device 14 pushing status data 27 to alarm management engine 12. Alarm fatigue calculator 40 may calculate alarm fatigue levels associated with respective users of user device 14 based on one or more user fatigue model 24 in user fatigue model database 18.

Alarm fatigue calculator 40 may feed the calculated alarm fatigue level to alarm condition calculator 42. Alarm condition calculator 42 may calculate alarm condition 44 for medical device 16 based on information from status data 27, alarm indicator 34, calculated alarm fatigue level, medical device model 28, and patient condition 32. In various embodiments, alarm condition 44 comprises instructions for alarms generated by medical device 16. The instructions can specify alarm attributes (e.g., alarm frequency, alarm threshold, alarm distribution mode (such as visual, auditory, sensory, tactile, etc.), alarm intensity (e.g., for a given distribution mode, how intensely the alarm is presented), alarm duration, alarm severity, etc.), alarm output interface (e.g., on user device 14, on a centralized alarm system, or medical device 16, etc.), measurement sensitivity, and any other parameter that affects likelihood of increased response to the alarms by one or more users whose alarm fatigue levels are considered in generating alarm condition 44.

Alarm condition 44 may be communicated to an adapter 46 located at applicable medical device 16. Adapter 46 may monitor and filter alarms from medical device 16 based on alarm condition 44. In some embodiments, medical device 16 and/or adapter 46 may generate and communicate alarm indicator 34 to alarm management engine 12. Alarm indicator 34 can provide feedback about alarm condition 44, which can be used in machine learning algorithms.

In some embodiments, status data 27 can indicate that an alarm has been falsely generated. Alarm management engine 12 can use the false alarm indication information to learn conditions that lead to false alarms generation. To achieve condition learning, embodiments of alarm management engine 12 can implement various machine learning algorithms. For example, some embodiments implement supervised learning techniques, such as Averaged One-Dependence Estimators (AODE), artificial neural network, Bayesian statistics, case-based reasoning, decision trees, inductive logic programming, Gaussian process regression, gene expression programming, group method of data handling, learning automata, learning vector quantization, logistic model tree, minimum message length, lazy learning, instance-based learning, probably approximately correct learning, ripple down rules, symbolic machine learning, sub-symbolic machine learning algorithms, support vector machines, random forests, ensembles of classifiers, bootstrap aggregating (bagging), boosting (meta-algorithm), ordinal classification, regression analysis, information fuzzy networks (IFN), and conditional random field. Suitable sources for machine learning systems include those available at www.scikit-learn.org), which offers numerous machine learning, data mining, and data analysis tools based on the Python computer language.

In other embodiments, alarm management engine 12 can also (e.g., alternatively, or additionally) implement unsupervised learning techniques, such as artificial neural network, data clustering, expectation-maximization algorithm, selforganizing map, radial basis function network, vector quantization, generative topographic map, information bottleneck method, association rule learning, Apriori algorithm, Eclat algorithm, Frequent Pattern (FP)-growth algorithm, hierarchical clustering, single-linkage clustering, conceptual clustering, partitional clustering, k-means algorithm, fuzzy clustering, Density-Based Spatial Clustering of Applications with Noise (DBSCAN), Ordering Points To Identify the Clustering Structure (OPTICS) algorithm, outlier detection, local outlier factor, reinforcement learning, temporal difference learning, q-learning, learning automata, Monte Carlo method, Sarsa, deep learning, deep belief networks, deep Boltzmann machines, deep convolutional neural networks, and deep recurrent neural networks.

In embodiments, one or more machine learning algorithms can be used to create a smart alarm management system that can develop rules for alarm generation. For example, alarm indicator 34 and/or status data 27 indicative of a false alarm can be aggregated over a period of time allowing a machine learning algorithm executing in alarm management engine 12 to learn when an alarm is more or less likely to be a false alarm. Over time, the algorithm can additionally learn when to prevent generation of an alarm based on historical information and trends learnt from alarm indicator 34 and status data 27. In another example, a smart alarm system could be used to determine whether an alarm should be generated based on data collected from plurality of medical device 16.

In some embodiments, alarm management engine 12 can implement one or more machine learning algorithms to develop prediction models for alarms. For example, alarm management engine 12 can provide a projected number of false alarms for a particular shift and it can take the calculated projected number of false alarms into account by creating rules for generating alarms throughout that shift.

In some embodiments, users can manually input status data to the system. For example, a user can report dreams or nightmares. A user can also report diet, exercise, and different types of ailments (e.g., if a user gets the flu, the user could report that to the system). In various embodiments, alarm management engine 12 can receive a variety of user-created status data inputs in status data 27 that may be used to create better (e.g., more productive, useful, etc.) user fatigue models 24.

In some embodiments, user fatigue model 24 is updated based on status data 27. Multiple user fatigue models 24 can be updated simultaneously or in sequence as status data 27 is received; in some embodiments, alarm management engine 12 may be limited in the updating by the number of users registered thereto. In some embodiments, incoming status data 27 can overwrite previously stored status data within user fatigue model 24; in other embodiments, incoming status data 27 can be stored along with previously stored status data to create a historical set of status data.

In various embodiments, the alarm fatigue level may be calculated based on previously updated user fatigue model 24. Alarm fatigue level can have a baseline and a current value. For example, one or more users might have a slowly increasing alarm fatigue level week over week. However, daily factors impacting the user can alter (e.g., add to or subtract from) the base line. For example, a base line can increase by 2% week over week. In another example, a user is alert with a reduced fatigue relative to the baseline in the morning, but after a 12 hour shift the user's fatigue level is heightened relative to that user's baseline. A baseline might be reset after vacation, for example.

A "default" user fatigue model 24 for a particular user can comprise the baseline in some embodiments. The baseline can be a historically determined "normal" fatigue level for the particular user based on samples collected during a day, a week, a particular shift, and/or a particular length of shift, all of which serve to determine an "un-fatigued" state. For example, as the day progresses, user fatigue model 24 can be updated based on various status data 27 received and the user's alarm fatigue level can subsequently be determined. As user fatigue model 24 of the corresponding user is updated, the alarm given to the user can be adapted accordingly. Consider a scenario where a user, say a nurse or doctor, has numerous long shifts. The disclosed system might discover that the user becomes fatigued with respect to alarms after more than 10 hours of shift on a consistent basis. The system discovers this condition by measuring the user's response time to alarms where the response time begins to increase measurably after 10 hours. Even though the user is responding within an acceptable period, the measured increase in response time can be considered as a leading indicator for fatigue. Discovery of this leading indicator can then be considered part of the specific user's baseline fatigue model in future settings. Further, such a measured indicator can also be incorporated into the fatigue models of other stakeholders having similar characteristics of the user; say all nurses or all doctors for example, if the measured indicator is validated for the class of users.

Using status data 27, some embodiments alarm management engine 12 can adapt and learn how quickly a particular user's alarm fatigue level increases over time given normal operating (e.g., working) conditions. Other factors that can be learned over time include how the user's alarm fatigue level changes after some number of days off, after a weekend, and/or after a night of sleep (e.g., where the user gets only 6 hours of sleep compared to when the user gets 10 hours of sleep).

In some embodiments, the alarm fatigue level can be categorized into different tiers, such as no alarm fatigue, low-level alarm fatigue, mid-level alarm fatigue, and high-level alarm fatigue. In other embodiments, the alarm fatigue level can be classified along a continuum. When alarm fatigue is classified along a continuum, alarms generated may be modified based on user fatigue model attributes 26 seen as contributing more to alarm fatigue levels. For example, if the particular user experiences alarm fatigue caused mainly by a high number of environment alarms, alarm management engine 12 can provide the user with specially tailored alarms. In another example, if the user has experienced a high number of alarms that incorporate particular sounds, the system can provide an alarm that includes a different set of sounds that may also incorporate tactile feedback and/or visual feedback. User fatigue attributes 26 can be weighted according to importance or strength of correlations in some embodiments. In some embodiments, alarm fatigue levels can be characterized on different scales, such as personalized fatigue level (e.g., specific to a particular user), a group level (e.g., specific to users working in a particular group), a "floor" level (e.g., specific to users working in a particular floor level of a building), a "shift" level (e.g., specific to users working in a particular shift), an institution level (e.g., specific to users working in a particular institution), etc. In some embodiments, alarm fatigue levels can have many dimensions beyond a tiered system. Such an approach can be considered advantageous, for example, because it allows the system to deliver alarms to the user where the alarm not only addresses the user's fatigue, but also provides an indication to the user that they are, in fact, suffering from fatigue based on the modality or nature of the alarm.

In a general sense, fatigue data can be classified into various types, examples include emotional fatigue, physical fatigue, or mental acuity fatigue. Each fatigue-type can be inferred based on status data 27. For example, mental acuity fatigue may be inferred by determining how long it takes the user to make a decision; physical fatigue may be inferred based on how long it physically takes the user to respond to an alarm or other activity (e.g., where response time can optionally be normalized based on distance traveled to respond to an alarm); etc. Each type of fatigue may correspond to a unique signature or template generated based on status data 27.

In various embodiments, alarm indicator 34 comprises an indication of a medical alert requiring a response from the user. In some embodiments, alarm indicator 34 may comprise inputs from medical device 16 that collect physiological information from the patient. When, for example, a medical sensor indicates a heart rate has flat lined, an alert condition is met. Alarm management engine 12 receives an indication of the alert condition through alarm indicator 34.

According to some embodiments, alarm management engine 12 may be capable of synthesizing and/or interpreting medical sensor data directly, and then determining whether an indication of a medical alert exists. In embodiments where the alarm management engine 12 is used with existing medical device 15, alarm management engine 12 may learn and/or adapt so that alarm condition 44 can be standardized (e.g., made uniform) and managed regardless of the legacy and/or default alarm conditions used by medical device 16. In some embodiments, learning models can be tied to patient condition 32, care setting, device type, device manufacturer, and other such parameters.

In various embodiments, alarm management engine 12 facilitates generating an alarm directed to a specific user taking into account the user's alarm fatigue level. In some embodiments, alarm management engine 12 additionally takes into account the alarm fatigue level of another user or users. In some embodiments, an alarm generation instruction is triggered by an indication of a medical alert from an outside source; thereafter, the alarm generation instruction is modified by one or more alarm fatigue levels; the modified alarm generation instruction generates the alarm. In various embodiments, alarm management engine 12 can take into account alarm fatigue levels of a single user; in other embodiments, alarm management engine 12 can take into account the alarm fatigue of a plurality of users. In various embodiments, alarm management engine 12 can also take into account alarm fatigue levels of non-users (e.g., persons outside the system may develop alarm fatigue, which can minimize the impact of the alarm based on the number of non-users potentially affected).

According to some embodiments, alarm management engine 12 can take into account instructions that specific users should receive only particular alerts (e.g., some recipients can only interpret sound alerts generated in a particular frequency range). In various embodiments, system 10 can be configured to comply with various regulations (e.g., governmental, administrative, and private) with which alarm systems must comply.

In some embodiments, when alarm fatigue level indicates no alarm fatigue, alarm condition 44 may permit various alarms to be generated (e.g., issued, created, sounded, etc.), for example, alarms based on sounds, vibrations, and/or a light, where the alarm corresponds to a "default" state. When alarm fatigue level indicates low-level alarm fatigue, alarm condition 44 may indicate a different alarm, for example, a specific combination of sounds, vibrations, and/or lights corresponding to the low-level alarm fatigue. Likewise, mid- and high-level alarm fatigue levels may correspond to respective alarm types, such as unique sounds, lights, etc. tailored to alarm fatigue levels of relevant users.

In some embodiments, the generated alarm may be distributed (e.g., disseminated, communicated, transmitted, sounded, etc.) based on alarm condition 44. Distribution can be carried out in a number of different ways. For example, each individual user may have a personal alarm device (e.g., watch) that is capable of conveying an alarm perceptible to the intended recipient. In some embodiments, the distributed alarm is directed to relevant users to the exclusion of others.

In an example scenario using embodiments of system 10, consider a hypothetical intensive care unit (ICU) of a hospital, which is manned by two nurses, Alice and Bob. At 8:00 AM, nurse Alice logs into user device 14 (e.g., computer) at a central hub in the ICU to begin her day's shift. Status data 27 logs the time of entry and communicates it with Nurse Alice's credentials to alarm management engine 12. Alarm fatigue calculator 40 calculates nurse Alice's user fatigue at level I (e.g., lowest level) based on user fatigue model 24 and user fatigue model attribute 26 determined from status data 27.

Assume that at 8:15 AM, a patient is brought into the ICU in serious condition. Nurse Alice registers the patient at the central hub and status data 27 indicative of the patient's condition is manually entered into user device 14 and received at alarm management engine 12. Nurse Bob logs into an electronic chart at the patient's bedside and enters information about medications being provided to the patient into the electronic chart. Information entered by nurse Bob along with nurse Bob's credentials are sent to alarm management engine 12. Assume that Nurse Bob is set to end his shift at 9:00 AM after 8 hours of continuous work at the ICU. Alarm fatigue calculator 40 calculates nurse Bob's user fatigue at level V (e.g., highest level) at the time of last receipt of status data 27 based on user fatigue model 24 and user fatigue model attribute 26 determined from status data 27.

Assume that medical device 16 substantially continuously measures the patient's blood pressure. A blood pressure reading at 8:16 AM indicates 130/90 mm Hg; at 8:20 AM indicates 120/80 mm Hg; and at 8:24 AM indicates 115/65 mmHg. Medical device model 28 corresponding to medical device 16 may specify that any blood pressure measurement over 120/80 mm Hg should generate an alarm. Patient condition 32 may specify that blood pressure for patients with a "serious" designation typically can vary beyond the normal range, but the rate of change is to be monitored more closely. Further in view of Bob's inferred high user fatigue level, generation of alarms may be tempered to only the more significant ones.

Alarm condition calculator 42 generates alarm condition 44 based on information from medical device database 20, patient conditions database 22 and user fatigue calculated by alarm fatigue calculator 40, and communicates alarm condition 44 to an adapter 46 located at medical device 16. Adapter 46 monitors and filters alarms from medical device 16. In the example, alarms may not be generated at medical device 16 for blood pressure readings at 8:16 AM and 8:20 AM; however, alarms may be generated at 8:24 AM in view of the rate of change of blood pressure. In some embodiments, alarms may be generated at 8:16 AM and communicated to nurse Alice's work station, as nurse Alice has a lower inferred fatigue level than nurse Bob, but not displayed visibly or audibly at nurse Bob's work station, whereas alarms generated at 8:24 AM may be communicated to both nurse Alice and nurse Bob. Medical device 16 and/or adapter 46 may generate alarm indicator 34 indicating that alarms have been generated and/or communicated (e.g., based on alarm condition 44). Such alarm indicator 34 can facilitate feedback and/or machine learning at alarm management engine 12.

In a general sense, alert management engine 12 of system 10 configured to perform various steps. First, alert management engine 12 receives status data 27 corresponding to a user, where status data 27 modifies at least one user fatigue model attribute 26. Second, alert management engine 12 updates corresponding user fatigue model 24 based on status data 27. Third, alert management engine 12 determines an alarm fatigue level based on updated user fatigue model 24. Fourth, alert management engine 12 generates alarm condition 44 targeting the user based on the calculated alarm fatigue level (among other parameters). Finally, adapter 46 modifies alarms generated at medical device 16 according to alarm condition 44 and distributes modified alarm 78 to the user.

In various embodiments, system 10 may facilitate aggregation and/or management of alarms in a consumable fashion. In some embodiments, adapter 46 associated with medical device 16 may comprise an alarm monitor, an alarm filter, an alarm modifier, a memory element for storing data, and a processor that executes instructions associated with the data. The processor and the memory element cooperate such that adapter 46 is configured for receiving alarm condition 44 from alarm management engine 12, receiving an alarm from medical device 16, modifying the alarm according to alarm condition 44 and generating alarm indicator 34 based on the modification. In some embodiments, alarm indicator 34 comprises a feedback to alarm management engine 12, and alarm condition 44 is further based on the feedback. Alarm condition 44 may be configured to increase a likelihood of the user responding to the modified alarm.

In some embodiments, alarm condition 44 is based on an alarm fatigue level of a user of medical device 16, the alarm fatigue level being based at least on medical device model 28 and patient condition 32. The alarm may be based on a physiological measurement of a patient by medical device 16. In some embodiments, modifying the alarm can include deleting the alarm based on alarm condition 44. In some other embodiments, modifying the alarm can include changing a format of the alarm. In yet other embodiments, modifying the alarm can include changing a distribution mode of the alarm.

Turning to the infrastructure of system 10, alarm management engine 12 can be embodied as computer executable instructions stored on one or more non-transitory computer-readable media (e.g. hard drives, optical storage media, flash drives, ROM, RAM, etc.) that, when executed by one or more processors, cause the processors to execute the functions and processes described herein. In some embodiments, alarm management engine 12 may execute in a distributed manner, portions of which are integrated into different adapters 46. For example, a portion of alarm management engine 12 that can calculate alarm condition 44 for medical device A may be integrated into adapter 46 corresponding to medical device A; another portion of alarm management engine 12 that can calculate alarm condition 44 for medical device B may be integrated into adapter 46 corresponding to medical device B; and so on. In other embodiments, alarm management engine 12 may execute in a centralized manner, calculating alarm condition 44 for a plurality of medical devices 16 and communicating alarm condition 44 over network 11 to relevant medical devices 16.

In some embodiments, alarm management engine 12 can be integrated into a single computing device or distributed among a plurality of computing devices (either locally or remotely located from one another) communicatively coupled via data exchange interfaces (e.g., short-range, long-range, wireless, wired, near-field communication, Bluetooth, Ethernet, Wi-Fi, USB, etc.), and/or connected via local or long-range networks (e.g. Internet, cellular, local-area networks, wide-area networks, intranets, etc.). In some embodiments, alarm management engine 12 can be embodied as one or more dedicated hardware computing devices specifically programmed (e.g. via firmware) to execute the functions and processes described herein.

In some embodiments, alarm management engine 12 can be incorporated into existing alarm management systems via installation of appropriate hardware and/or software updates associated with the functions described herein. For example, one suitable alarm management system is NantHealth's Magellan™ or cOS™ system, including functionalities as described herein.

Figure 2:
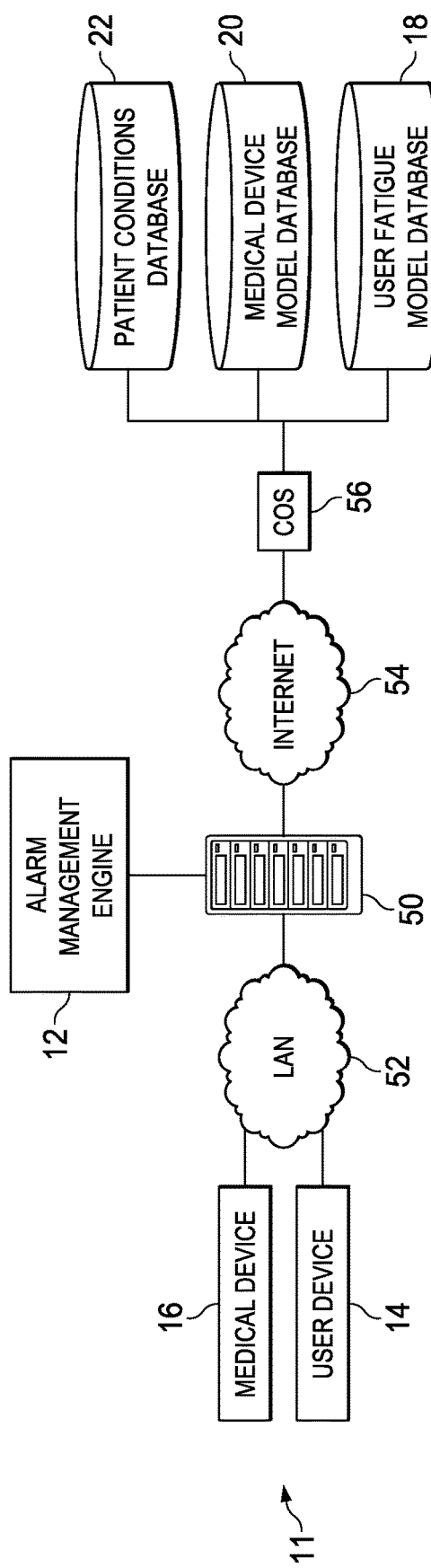
FIG. 2 is a simplified block diagram illustrating example details of the system according to an embodiment.

Turning to FIG. 2, FIG. 2 is a simplified block diagram illustrating network 11 according to an example embodiment of system 10. Alarm management engine 12 may execute in a server 50 connected over a local area network 52 with medical device 16 and user device 14. Server 50 may connect over Internet 54 to a clinical operating system (cOS) 56 that may communicate with user fatigue model database 18, medical device model database 20 and patient conditions database 22. Note that LAN 52 and Internet 54 may be connected over a router (not shown) situated at an edge of LAN 52. In some embodiments, LAN 52 may comprise a portion of an enterprise network.

In various embodiments, cOS 56 integrates clinical, financial, operational and environmental data into a single platform. In various embodiments, cOS 56 comprises a cloud-based platform for patient records, medical devices, imaging systems, financial systems, costing systems, evidence-based clinical pathways, and personalized genomic and proteomic data. cOS 56 combines and organizes pertinent medical information for easy access and utilization at the point of care. In various embodiments, alarm management engine 12 may connect to cOS 56 over Internet 54, and access user fatigue model 24, patient condition 32, medical device model 28, etc. through cOS 56. cOS 56 can facilitate privacy of health records, appropriate authentication, and other security measures consistent with various health care privacy related laws and regulations. For example, alarm management engine 12 may establish a secure tunnel with cOS 56 to access user fatigue model database 18, medical device model database 20 and patient conditions database 22.

In some embodiments, server 50 may comprise a physical computing device, such as a desktop server. In other embodiments, server 50 may execute in a rack server, for example, in a computing station located remotely from medical device 16 and user device 14, but nevertheless in communication with medical device 16 and user device 15 over LAN 52. LAN 52 may include switches and other network elements that can facilitate wired or wireless communication between medical device 16, user device 14 and alarm management engine 12.

Figure 3:
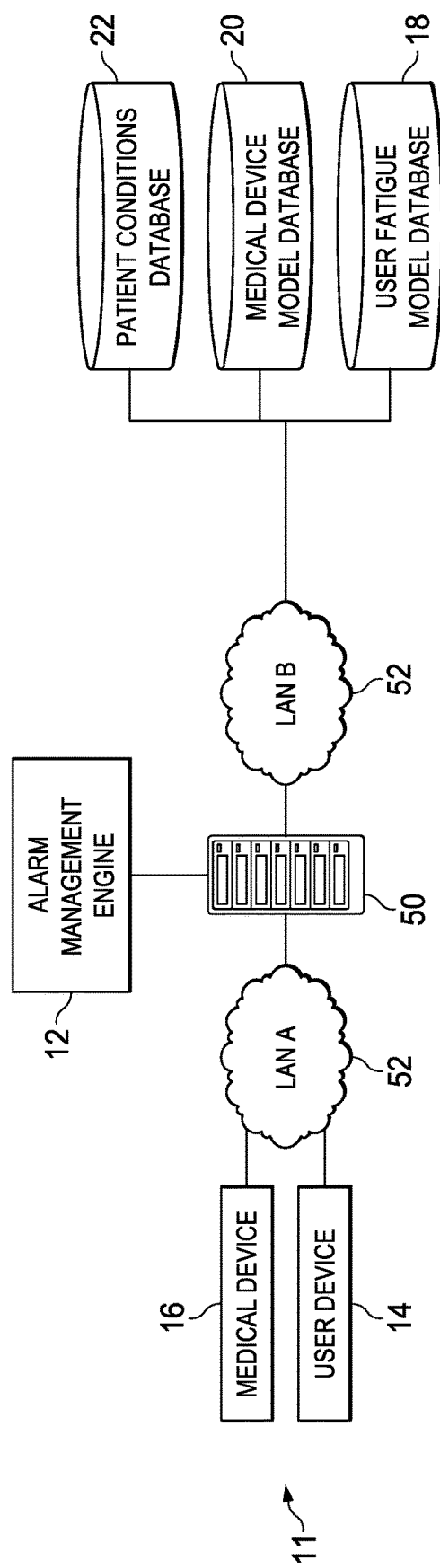
FIG. 3 is a simplified block diagram illustrating other example details of the system according to an embodiment.

Turning to FIG. 3, FIG. 3 is a simplified block diagram illustrating network 11 according to another example embodiment of system 10. Alarm management engine 12 may execute in a server 50 connected over a first local area network 52 (LAN A) with medical device 16 and user device 14. Server 50 may connect over a second local area network 52 (LAN B) to user fatigue model database 18, medical device model database 20 and patient conditions database 22. In some embodiments, LAN A and LAN B may comprise the same LAN; in other embodiments, LAN A and LAN B may comprise separate portions of an enterprise network; in yet another embodiment, LAN A and LAN B may comprise separate enterprise networks linked together by appropriate secure network elements, such as switches and routers; in yet other embodiments, LAN A and LAN B may comprise virtual local area networks (VLANS) of an enterprise network.

Note that various implementations of LAN A and LAN B may be encompassed by the broad scope of the embodiments. In one example embodiment, LAN A and LAN B may be connected over a wireless network. In another embodiment, LAN A and LAN B may be connected over the Internet (or other WAN), but through secure tunnels and/or other network security measures tailored to transparently and seamlessly cause LAN B to appear to belong to the same network as LAN A. For example, user fatigue model database 18, medical device model database 20 and patient conditions database 22 may be stored and/or implemented in LAN B, comprising a data center network geographically or physically separate from LAN B, comprising a hospital network, but nevertheless connected to LAN A through appropriate communication channels.

Figure 4:
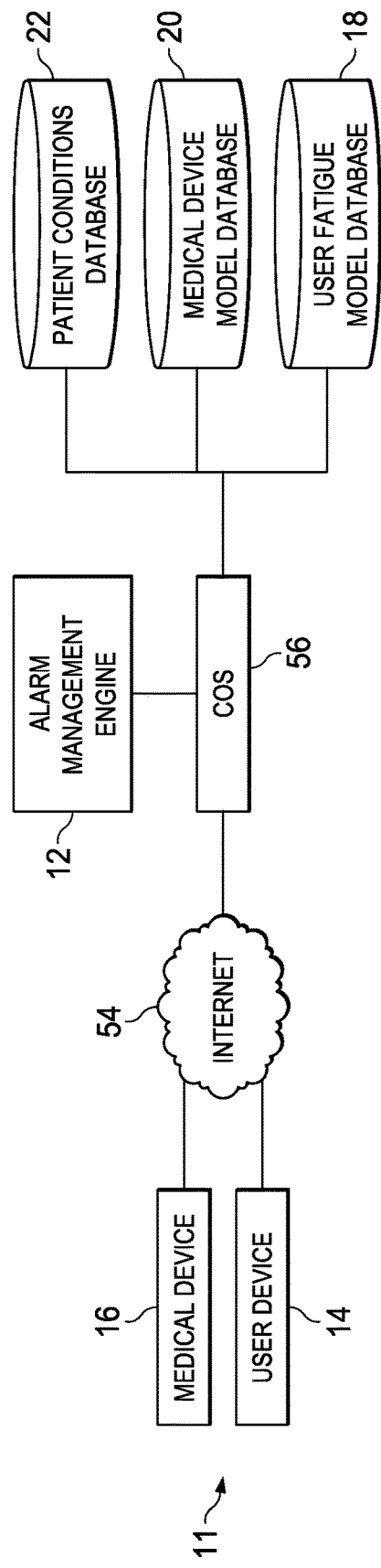
FIG. 4 is a simplified block diagram illustrating yet other example details of the system according to an embodiment.

Turning to FIG. 4, FIG. 4 is a simplified block diagram illustrating network 11 according to yet another example embodiment of system 10. Alarm management engine 12 may communicate with medical device 16 and user device 14 across Internet 54 through cOS 56. For example, cOS 56 may execute in a cloud network and receive status data 27, alarm indicator 34, etc. from medical device 16 and user device 14, communicate them with alarm management engine 12, and facilitate access by alarm management engine 12 of user fatigue model database 18, medical device model database 20 and patient conditions database 22 stored/implemented in the cloud. In some embodiments, alarm management engine 12 may execute in a server communicatively coupled to cOS 56; in other embodiments, alarm management engine 12 may execute in a same server as cOS 56. In some embodiments, user fatigue model database 18, medical device model database 20, and patient conditions database 22 may be implemented in a separate storage area network (SAN) that is communicatively coupled to cOS 56 and/or alarm management engine 12.

Figure 5:
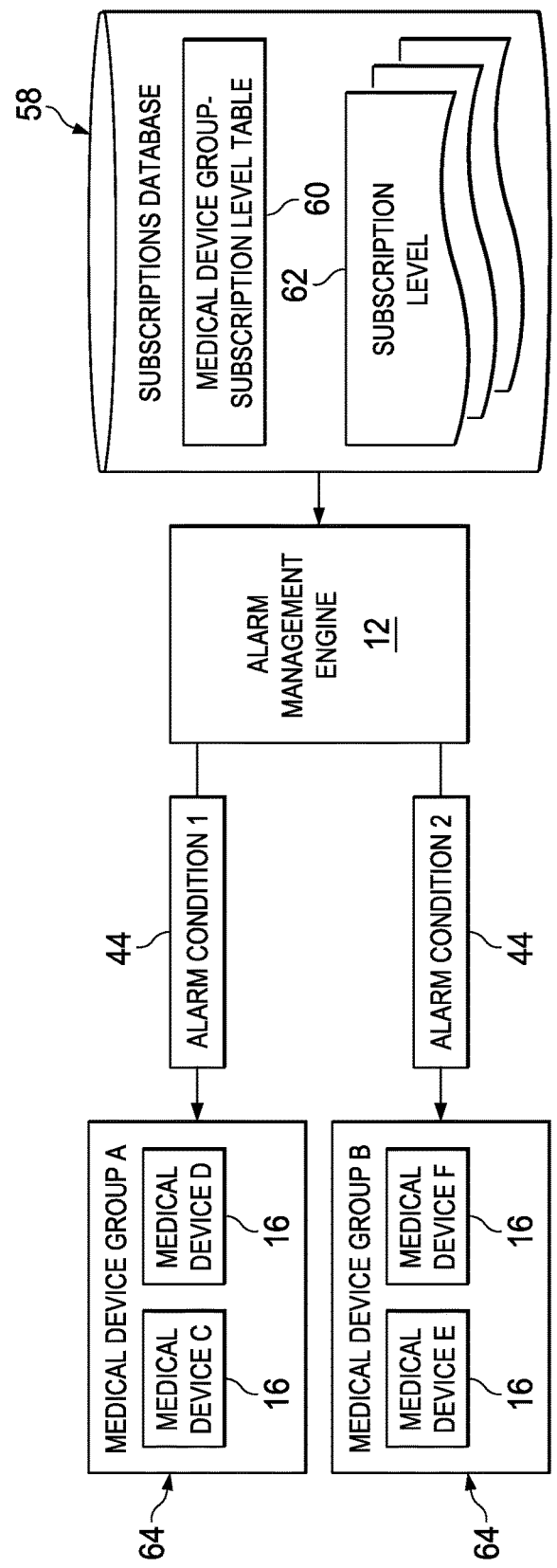
FIG. 5 is a simplified block diagram illustrating yet other example details of the system according to an embodiment.

Turning to FIG. 5, FIG. 5 is a simplified block diagram illustrating another example embodiment of system 10. In some embodiments, alarm condition 44 may be provided based on subscriptions to an alarm service. A subscriptions database 58 may be communicatively coupled to alarm management engine 12. Subscriptions database 58 may include a medical device group-subscription level table 60 and subscription levels 62. A plurality of medical device 16 may be grouped into separate medical device groups 64. Alarm management engine 12 may access medical device group-subscription level table 60 in subscriptions level database 58 and generate alarm condition 44 based on subscription levels 62 (in addition to other parameters as already discussed herein).

For example, medical devices C and D may be grouped into medical device group A; medical devices E and F may be grouped into medical device group B. Medical device groups 64 may be classified (e.g., grouped) according to any suitable grouping attribute. For example, the grouping attribute may comprise location of medical device 16: medical device group A may correspond to medical devices located in an ICU of a hospital; medical device group B may correspond to medical devices located in an outpatient clinic of the hospital. In another example, the grouping attribute may comprise device types: medical device group A may correspond to heart monitors; medical device group B may correspond to blood pressure monitors. In yet another example, the grouping attribute may comprise departments: medical device group A may comprise medical devices belonging to the oncology department; medical device group B may comprise medical devices belonging to the emergency room department. Virtually any suitable grouping attribute may be included within the broad scope of the embodiments.

Each medical device group 64 may subscribe to different subscription levels 62. Each subscription level 62 may specify certain types of alarm condition 44; certain types of analyses used to generate alarm condition 44; certain attributes (e.g., parameters, variables, etc.) to be taken into consideration to compute alarm condition 44; etc. Virtually any suitable differentiator of alarm condition 44 may be included in subscription level 62 within the broad scope of the embodiments.

During operation, assume, merely for example purposes and not as a limitation, that alarm management engine 12 generates alarm condition O for identical medical devices C and E based on alarm fatigue levels, medical device model 28, patient condition 32, etc., as described herein. Assume that alarm condition 0 indicates that alarms are to be generated for users P and Q only when a patient's blood pressure crosses 130/90 mm Hg.

Alarm management engine 12 may access subscriptions database 58 to determine subscription level 62 corresponding to medical devices C and E. For example, alarm management engine 12 may determine (e.g., from preconfigured information, polling medical devices C and E, or other appropriate methods) that medical device C belongs to medical device group A and medical device E belongs to medical device group B. From medical device group-subscription level table 60, alarm management engine 12 may determine that medical device group A subscribes to subscription level G, which indicates that alarm signals be communicated in a vibratory mode to specific user devices such as watches (according to subscription level 62) and medical level group B subscribes to subscription level H, which indicates that alarm signals be communicated audibly and visually on the medical device itself.

Alarm management engine 12 may modify alarm condition Oto alarm condition 1 for medical device C based on information from subscriptions database 58; and modify alarm condition Oto alarm condition 2 for medical device E. Thus, alarm condition 1 may indicate that alarms are to be generated for users P and Q only when the patient's blood pressure crosses 130/90 mm Hg and the users are to be notified via vibratory mode to specific user devices; alarm condition 2 may indicate that alarms are to be generated for users P and Q only when the patient's blood pressure crosses 130/90 mm Hg and the alarms are to be audibly and visually activated at medical device E.

Figure 6:
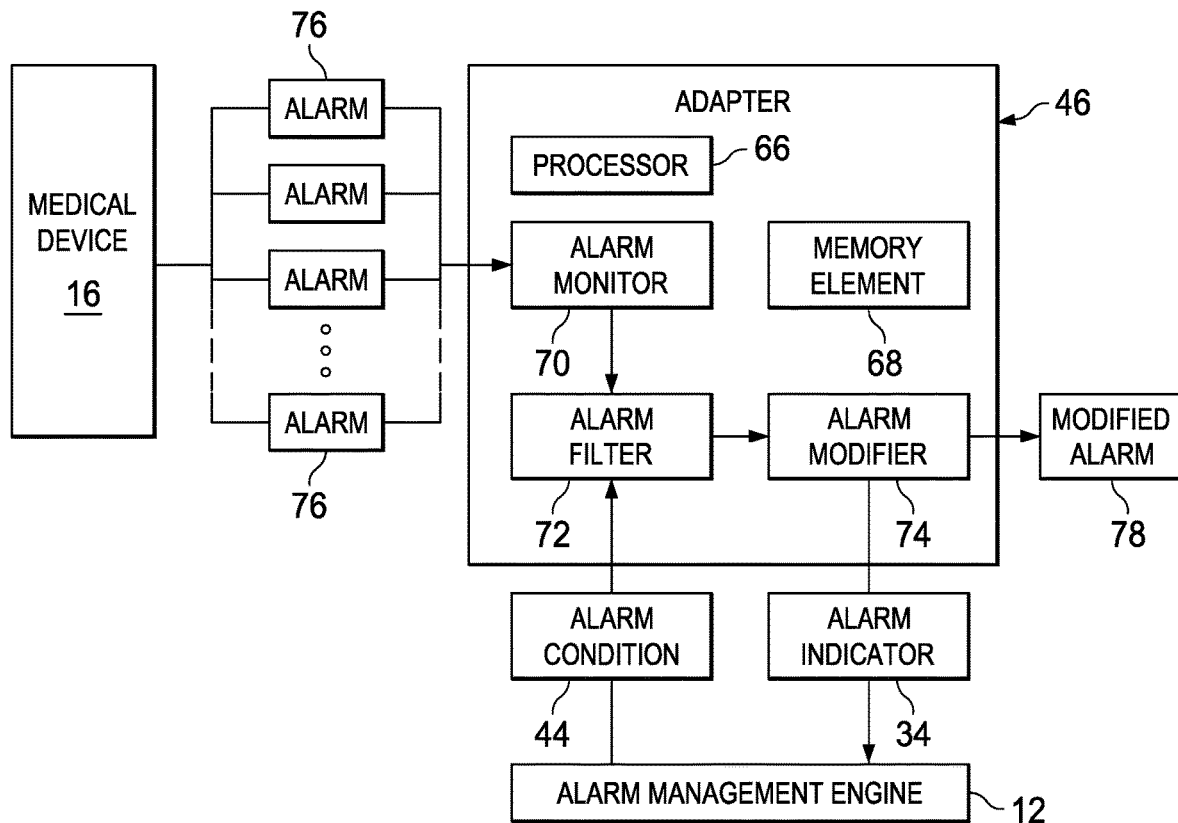
FIG. 6 is a simplified block diagram illustrating yet other example details of the system according to an embodiment.

Turning to FIG. 6, FIG. 6 is a simplified block diagram illustrating example details according to an example embodiment of system 10. Adapter 46 may be communicatively coupled to medical device 16 and alarm management engine 12. In some embodiments, adapter 46 may be remote from medical device 16 and communicate wirelessly with medical device 16. In other embodiments, adapter 46 may be detachably attached (e.g., through universal serial bus (USB) or other such electrical connectors) to medical device 16. In yet other embodiments, adapter 46 may be permanently attached to medical device 16. In yet other embodiments, adapter 46 may comprise a separate physical appliance (e.g., component) embedded inside a chassis of medical device 16 and integrated therein. In yet other embodiments, adapter 46 may comprise an inseparable component integrated into a hardware of medical device 16; for example medical device 16 could integrate a Digi Connect ME® device that has been configured or programmed according to the disclosed techniques.

In yet other embodiments, adapter 46 may comprise a software application executing inside medical device 16. In yet other embodiments, adapter 46 may comprise a software application executing in a computing device separate from medical device 16 and communicatively coupled thereto (e.g., connected via Ethernet links, connected through a controller, etc.). For example, adapter 46 may comprise a software application (e.g., software container, object, module, etc.) executing alongside (e.g., with, concurrently, etc.) alarm management engine 12 in the same server.

Adapter 46 may include a processor 66, a memory element 68, an alarm monitor 70, and an alarm filter 72, an alarm modifier 74. Adapter 46 may receive alarm condition 44 from alarm management engine 12. Alarm condition 44 may be based on an alarm fatigue level of a user of medical device 16, the alarm fatigue level being based on (among other parameters), user fatigue model 24, medical device model 28 and patient condition 32.

Adapter 46 may also receive one or more alarms 76 generated by medical device 16. In some embodiments, alarm 76 can comprise electrical signals; in other embodiments, alarm 76 can comprise visual, auditory, vibratory and other kinds of signals; in yet other embodiments, alarm 76 can comprise a signal indicative of an alarm; in yet other embodiments, alarm 76 comprises signals instructing an alarm to be generated. Alarm monitor 70 at adapter 46 is configured to receive and identify alarms 76. For example, alarm 76 comprises an electrical signal and alarm monitor 70 may comprise an electrical component configured to change its property upon receipt of the electrical signal. In another example, alarm 76 comprises an audible signal, and alarm monitor 70 may comprise a microphone sufficiently sensitive to pick up the audible signal. In yet another example, alarm signal comprises an optical signal, and alarm monitor 70 may comprise a light sensitive component that may activate upon receipt of the optical signal. Virtually any suitable type of alarm monitor 70 that can interface with alarms 76 may be used within the broad scope of the embodiments.

In various embodiments, adapter 46 modifies alarms 76 to modified alarm 78 according to alarm condition 44. Note that alarm condition 44 may be configured to increase a likelihood of the user (of medical device 16) responding to modified alarm 78 (e.g., relative to a likelihood of the user responding to alarms 76). Modification may comprise filtering alarms 76 to delete some of alarms 76 based on alarm condition 44 (e.g., alarm condition 44 may specific alarms once every 10 minutes so that any alarms generated in the intervening 9 minutes are discarded); modification may comprise altering a format of alarms 76 (e.g., changing a vibratory format to a visually blinking format; changing a text message alarm to a beeping sound alarm; changing alarm 76 comprising an alarm instruction to a vibration on the user's wearable device; etc.). In some embodiments, modification may comprise changing a distribution mode of alarms 76. For example, alarms 76 may comprise a blinking light on medical device 16; modified alarm 78 may comprise a text message on cell phones of a plurality of registered users.

In some embodiments, modification of alarms 76 may be accomplished by alarm filter 72 and alarm modifier 74. Alarm filter 72 is configured to filter alarms 76 according to alarm condition 44. For example, medical device 16 may generate alarms 76 indiscriminately whenever certain manufacturer preconfigured alert conditions are met. On the other hand, alarm condition 44 may be tailored to specific users, environments, etc. taking into consideration alarm fatigue levels, and other factors as described herein. Accordingly, alarm filter 72 may reduce the number of alarms; change the type of alarms; or otherwise generate instructions to change alarms 76 in a suitable manner according to alarm condition 44. In some embodiments, alarm filter 72 may take as inputs signals corresponding to alarms 76 from alarm monitor 70 and alarm condition 44 from alarm management engine 12 and produce as output instructions to generate modified alarm 78.

Alarm modifier 74 may generate modified alarm 78 according to the instructions from alarm filter 72. In some embodiments, each modified alarm 78 may also cause generation of alarm indicator 34, which may be sent back to alarm management engine 12 (e.g., as feedback). In some embodiments, alarm indicator 34 may be used to compute alarm condition 44.

Figure 7:
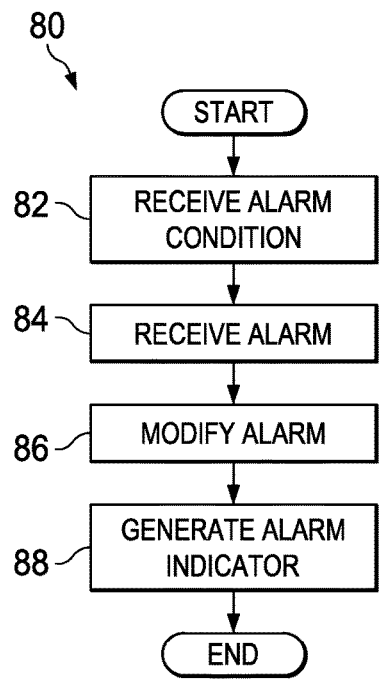
FIG. 7 is a simplified flow diagram illustrating example operations that may be associated with an embodiment of the system.

Turning to FIG. 7, FIG. 7 is a simplified flow diagram illustrating example operations 80 that may be associated with adapter 46 according to an embodiment of system 10. At 82, adapter 46 receives alarm condition 44 from alarm management engine 12. In some embodiments, alarm condition 44 is based on an alarm fatigue level of a user of medical device 16, the alarm fatigue level based on at least user fatigue model 24, medical device model 28, and patient condition 32. At 84, adapter 46 receives alarm 76 from medical device 16. At 86, adapter 46 modifies alarm 76 to generate modified alarm 78. In various embodiments, alarm condition 44 is configured to increase a likelihood of the user responding to modified alarm 78. At 88, adapter 88 generates alarm indicator 34 based on the modification.

Figure 8:
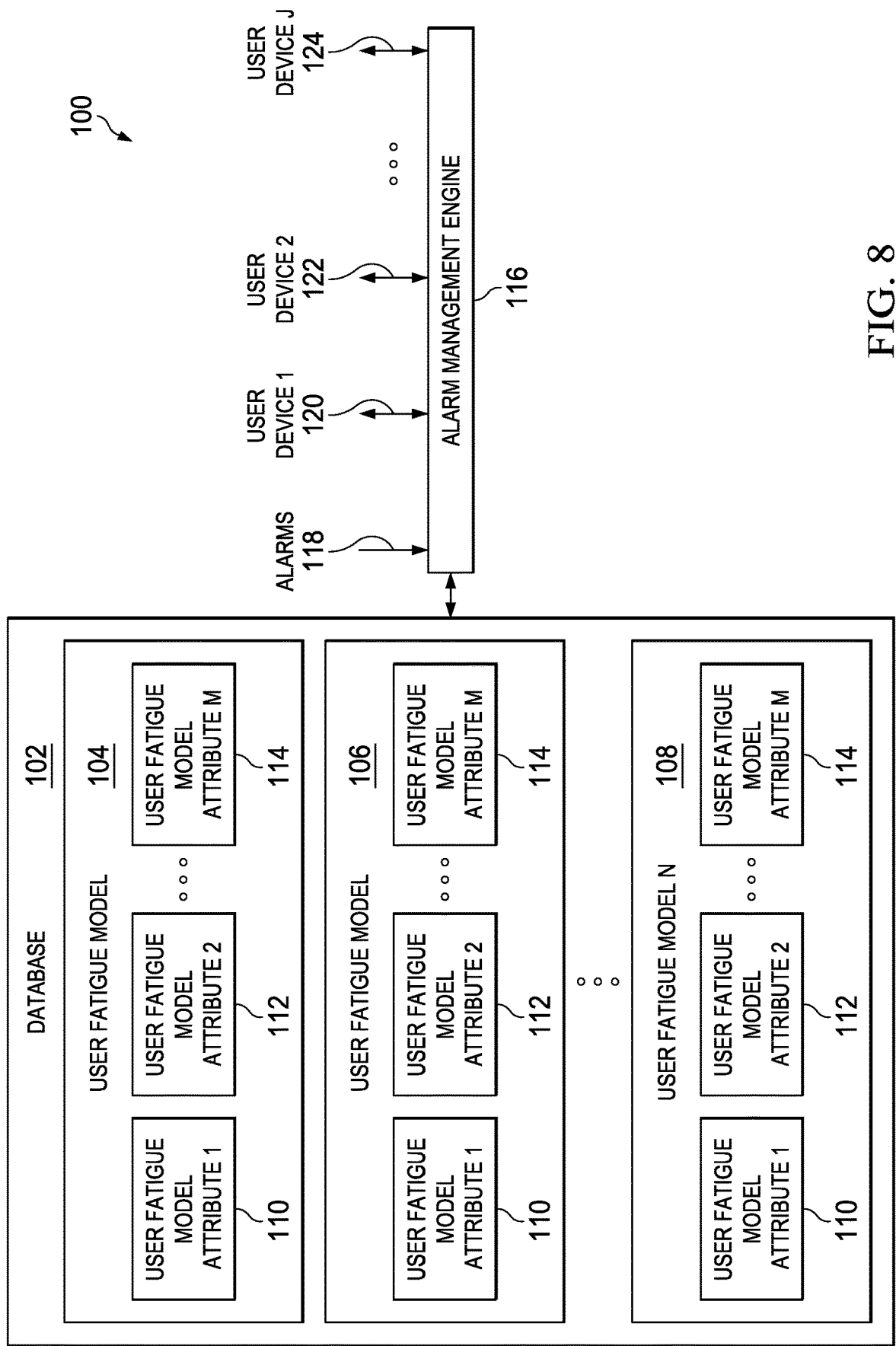
FIG. 8 is a simplified block diagram illustrating yet other example details of the system according to an embodiment.

Turning to FIG. 8, FIG. 8 is a simplified block diagram illustrating example details of a system 100 for alarm fatigue management. System 100 includes two components: a database 102, which can be stored either locally or remotely, and an alarm management engine 116. Database 102 can include N user fatigue models 104, 106, 108, where N is an integer value corresponding to the number of users within system 100. Each user fatigue model can include one or more user fatigue model attributes. User fatigue model 104 holds, for example, M user fatigue model attributes 110, 112, and 114, where M is an integer value corresponding to the number of attributes held in the user fatigue model.

Alarm management engine 116 can receive alarm indications via input 118, and it can additionally communicate with J number of user devices where J is an integer value corresponding to the number of user devices used with system 100.

Alarm management engine 116 can be embodied as computer executable instructions stored on one or more computer-readable media (e.g. hard drives, optical storage media, flash drives, ROM, RAM, etc.) that, when executed by one or more processors, cause the processors to execute the functions and processes of the inventive subject matter.

In some embodiments, alarm management engine 116 can be integrated into a single computing device or distributed among a plurality of computing devices (either locally or remotely located from one another) communicatively coupled via data exchange interfaces (e.g., short-range, long-range, wireless, wired, near-field communication, Bluetooth, Ethernet, Wi-Fi, USB, etc.), connected via local or long-range networks (e.g. Internet, cellular, local-area networks, wide-area networks, intranets, etc.). In some embodiments, alarm management engine 116 can be embodied as one or more dedicated hardware computing devices specifically programmed (e.g. via firmware) to execute the functions and processes of the inventive subject matter.

In some embodiments, alarm management engine 116 can be incorporated into existing alarm management systems via the installation of required hardware and/or software updates associated with the functions of the inventive subject matter. For example, one suitable alarm management system is NantHealth's Magellan™ of cOS™ system.

User fatigue model attributes can be considered to be factors or characteristics that can affect a user's fatigue level. User fatigue model attributes can include many different types of information, including information conveyed via the status data and information that is set based on details about a particular user. These attributes can be changed and/or updated periodically or continuously, depending on the sampling frequency in an embodiment. Additionally, the attributes can contain historical data rather than repeatedly updating a single piece of information.

Some examples of user fatigue model attributes include personality factors and physiological factors. Personality factors are factors that might indicate a person is more or less prone to alarm fatigue (e.g., irritability, psychological disorders, and personality type). Physiological factors can include factors that pertain to a certain user's physical abilities (e.g., deafness, blindness, color blindness, sensitivity to particular light and/or sound patters, and varying degrees of disabilities related to these conditions and others).

In some embodiments, system 100 comprising database 102 and alert management engine 116 can modify operating parameters of medical devices to help reduce alarm fatigue at the sensor level. In this aspect, each user fatigue model 104-108 is associated with a corresponding user, and alert management engine 116 is configured to perform the following steps. It receives user status data that includes at least one status attribute. It receives patient status data from one or more medical devices where the medical devices have at least one an alarm condition parameter. It updates the first user's user fatigue model based on the first user's status data. It determines an alarm fatigue level based on the updated first user fatigue model. It modifies the at least one operational parameter of the at least one medical device based on at least the alarm fatigue level of the user.

Figure 9:
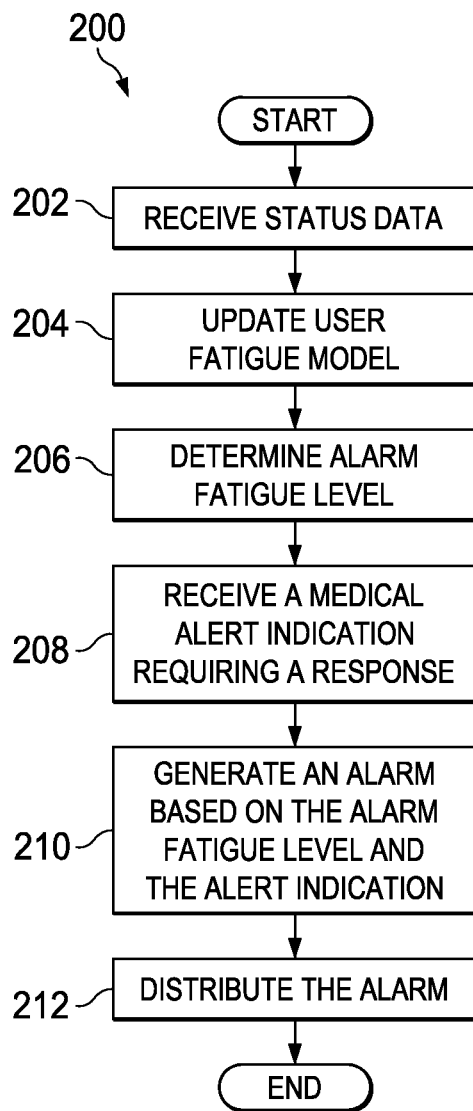
FIG. 9 is a simplified flow diagram illustrating other example operations that may be associated with an embodiment of the system.

Turning to FIG. 9, FIG. 9 is a simplified flow diagram illustrating example operations 200 that may be associated with alarm management engine 116 according to some embodiments of system 100. In step 202, alarm management engine 116 receives status data. Status data collected in step 202 can take many different forms, including physiological data, user shift data, and environmental alarm data. In step 204, a user fatigue model is updated based on the status data received in step 202. Multiple user fatigue models can be updated simultaneously or in sequence as the data arrives—the system is limited in this respect by the number of users accounted for in the system. Additionally, incoming status data can either overwrite previously stored status data within a user fatigue model or it can be stored alongside all previously stored status data to create a historical set of status data. In step 206, an alarm fatigue level is determined based on the previously updated user fatigue model of step 204. In step 208, system 100 receives an indication of a medical alert requiring a response from a user. The system can receive inputs from medical sensing equipment that collect physiological information from a patient. When, for example, a medical sensor indicates a heart rate has flat lined, an alert condition is met. In step 210, system 100 generates an alarm directed to a user taking into account that user's alarm fatigue level. In step 212, system 100 distributes the generated alarm based on the alarm fatigue level of step 206 and the indication of an alert of step 208.

Figure 10:
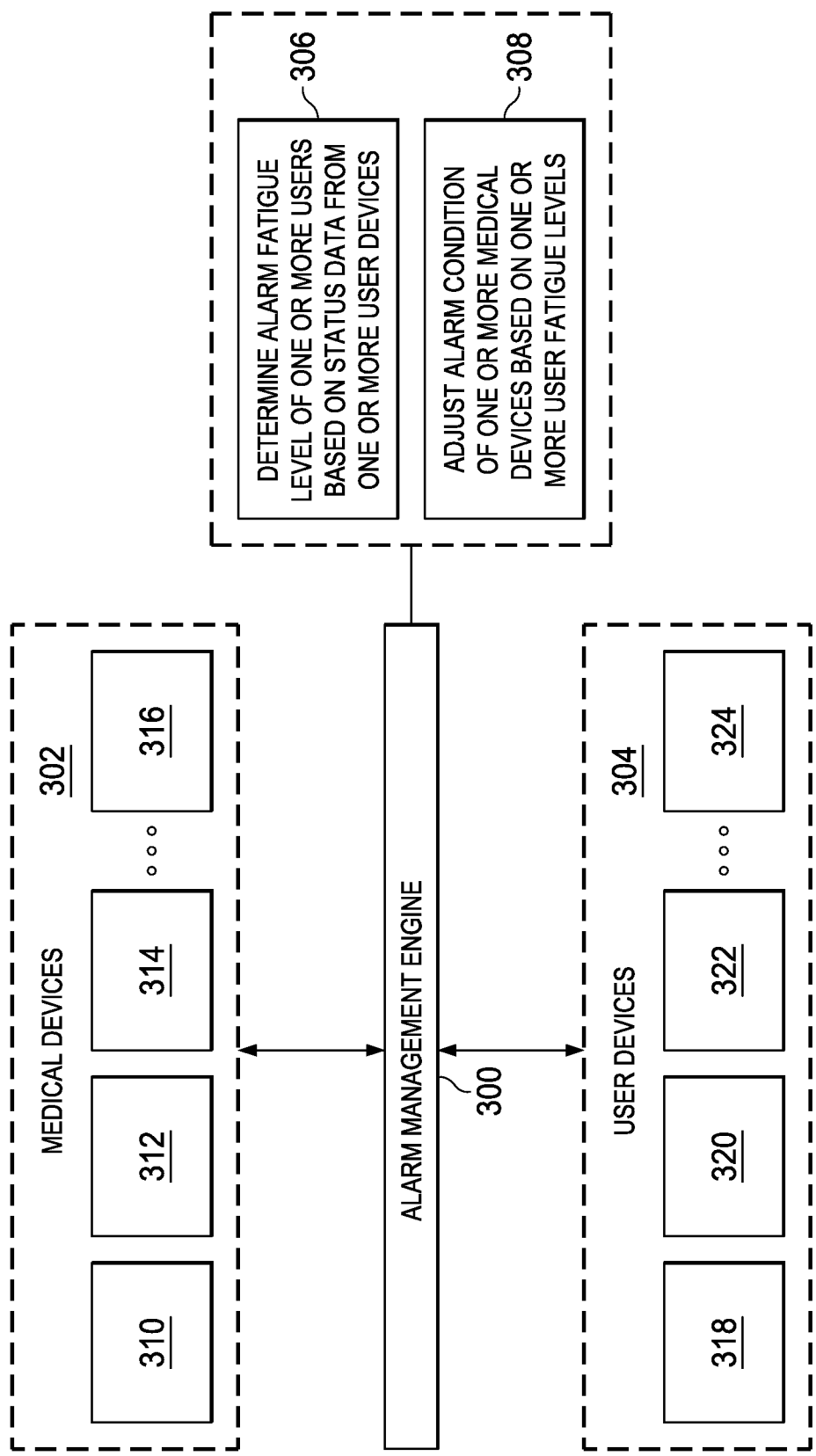
FIG. 10 is a simplified diagram illustrating example details according to an embodiment of the system.

Turning to FIG. 10, FIG. 10 is a simplified diagram illustrating example details and operations that may be associated with embodiments of system 100. An alarm management engine 300 performs step 306 by determining alarm fatigue based on status data collected from one or more medical devices 302 and performs step 308 by adjusting alarm conditions of one or more medical devices 302 based on the one or more user fatigue levels. In some embodiments, instead of simply altering alarms based on user fatigue levels, alarm management engine 300 is configured to alter alarm conditions of one or more medical devices 302. An advantage of altering alarm conditions of a medical device is that each individual device 310, 312, 314, 316 can be modified to indicate an alarm based on one or more nonstandard operational parameters. For example, if a particular medical device is prone to issuing excessive alarms because a threshold for meeting an alarm condition is too low (e.g., when a heart rate drops below 50 BPM, an alarm condition is met), the threshold comprising the alarm condition can be altered (e.g., such that the alarm condition is met only when the heart rate drops below 30 BPM), thus reducing a number of alarms generated by that particular medical device.

In some embodiments, the alarm condition can comprise a threshold value for the patient status data, for example, above which the medical device generates an alarm. For example, if the medical device is a heart rate monitor and it is originally configured to generate an alarm if a patient's heart rate drops below 50 BPM, then system 100 can modify the medical device to generate the alarm only when that patient's heart rate drops below 30 BPM.

In some embodiments, the alarm condition can comprise a maximum frequency at which the medical device can generate an alarm (or indication of an alert). For medical devices that detect physiological information that changes very slowly, it can be advantageous to permit the medical device to only generate an alarm every so often. For example, if a patient's body temperature drops below a threshold where the medical device will generate an alarm, the slow changing nature of body temperature may result in fluctuation about that threshold level. These fluctuations can in turn cause the medical device to generate many alarms very quickly as the patient's body temperature changes right around the threshold temperature. System 100 can remedy this by altering the alarm condition of the medical device such that it can generate an alarm only once every 10 minutes, which would allow the patient's body temperature to change without generating unnecessary alarms.

In some embodiments, the alarm condition can comprise a sampling frequency of a medical device. Thus, changing the alarm condition can change how frequently the medical device gathers physiological information from a patient.

This can be advantageous in that it can reduce the number of alarms the medical device generates.

In some embodiments, the alarm condition can comprise measurement sensitivity, which can determine a minimum amount of change a physiological measurement undergoes before the medical device will detect that change. This can also help to reduce unnecessary alarm generation. In an example, if a medical device is set to detect body temperature changes only when the temperature change is 0.2 degrees or greater, fewer alarms would be generated based on small fluctuations around the threshold value.

The same concepts can be extended to any type of medical device. Medical devices can include devices that directly measure physiological information, or machines that conglomerate that type of information (e.g., Phillips IntelliVue Patient Monitor and other comparable systems known in the art). Physiological quantities that can be measured by medical devices include: monitoring for cardiac problems such as arrhythmias (e.g., atrial, fibrillation, ventricular fibrillation, ventricular tachycardia, and premature ventricular contractions) and asystole (i.e., lack of measurable electrical cardiac activity); monitoring for pulse rate problems such as tachycardia and bradycardia; monitoring for respiration problems (for example, via oximetry) such as apnea, tachypnea, and desaturation; and monitoring for blood pressure problems such as hypertension and hypotension. Alarm conditions can correspond to a particular ECG waveform, or to an elevated blood toxin level in some embodiments. In some embodiments, alarms can include the physiological measurements thereby conveying information to the recipient while simultaneously alerting the recipient that a response is required.

Several medical devices may operate concurrently in a Medical Intensive Care Unit (MICU) and Coronary Care Unit (CCU). For example, a ventilator and Swan-Ganz catheter (a flexible tube inserted through the right side of the heart that monitors pressures and outflow from the heart) can both generate alarms when the devices measure status data that meets respective internal alarm conditions. Any medical device connected to alarm management engine 300 can be modified suitably to change the alarm condition within the medical device itself. The result is a reduced number of alarms in the course of normal operation of system 100, thereby decreasing overall alarm fatigue of one or more system users.

Alternatively, alarms can be distributed over a centralized system, for example, via alarm devices that are fixed in place throughout a hospital. The alarm devices can be capable of projecting lights of different colors and intensities, as well as sounds of different frequencies and intensities. One possible alarm device comprises a monitor such as a television with accompanying speakers where a distributed alarm can be presented as text, light, and/or sound. In some embodiments, system 100 can operate using an existing alarm system. System 100 can use the alarm distribution capabilities of the existing system to distribute its alarms. Regardless of the distribution method, in one way or another distribution of alarms will likely affect users beyond merely the target user. However, since the system is continually (or continuously) collecting status data from a plurality of users, these effects are taken into account in terms of each user's fatigue level.

Some embodiments of alarm management system 100 can operate in real-time, monitoring relevant user activities as they occur and using the monitoring information to adjust its output. To do so, system 100 employs a feedback loop. Status data updates a profile, which is used to determine alarm fatigue level to generate an output, which in turn influences the alarm fatigue level. For example, as a user experiences more and more alarms throughout a shift, that user's alarm fatigue rises. System 100, sensing and quantifying a rise in alarm fatigue level, modulates its alarm outputs to that user to mitigate the effects of that user's alarm fatigue.

Thus, a closed-loop control system (e.g., a proportional-integral-derivative control system) can be implemented to manage changes in alarm outputs. Closed-loop control systems can be under-damped, over-damped, or critically damped. System 100 can be configured to account for any hysteresis of its feedback loop, where hysteresis indicates a dependence of the output of system 100 on its current input and its history of past inputs. In other words, system 100 may compensate for possible staleness of data when contemplating how quickly that data can be used to influence output. To this end, system 100 can maintain frames of reference in its database for alarm fatigue levels that can span hours, days, weeks, months, and/or years.

One should also appreciate that system 100 is also able to monitor trends in available data in order to trigger shifts in how alarms are to be presented. The trends could be with respect to alarm data, user behavior data, or other types of data. System 100 can, in some embodiments, represent the trends as derivatives or rates of change of one value versus a second value; dx/dy for example. It should be appreciated that the derivatives or rates can be empirically measured across appropriate corresponding units of measure. For example, the rate of change could be missed alarms per day where number of alarms missed could be measured as a difference from one day to the next. More interesting examples might include a derivative associated with other values besides time. As an example, consider a scenario where the severity of an alarm (S) might correlated with number of missed alarms (M) for a specific individual. In such a scenario, dS/dM could be indicative of how well a user deals with alarm severity and that the user's a fatigue model should include triggers for such measures.

Beyond merely measuring trends as first order derivatives, it should be appreciated the trends could also include higher order derivatives of the available, measurable metrics. As system 100 collects data over time, system 100 can monitor the higher order derivatives to determine if one or more users are becoming fatigue at a faster rate for example. Returning to the example of missed alarms per unit time (dM/dt), system 100 can be configured to accept a constant rate at which the alarms are missed, at least to with a threshold. Note that when dM/dt is constant, its higher derivatives are zero; d2M/dt 2=0. However, should the higher order derivatives shift to unacceptable non-zero values (e.g., much greater than zero), then the system can begin altering its alarm strategy to address the possible indication that the user has become fatigued. The reader is reminded that the technique can also be leveraged for higher order rates of changes that do not involve time; d2x/dy2, d 3x/dy3, d 4x/dy4, etc.

In some embodiments, system 100 can generate recommendations as to what actions a user can/should take to reduce alarm fatigue levels (e.g., take a day off or generate a new work schedule). However, there is a difference between what system 100 would recommend versus what might be practical. For example, if a floor is short staffed, system 100 may be configured to consider a certain alarm fatigue level that is different from the alarm fatigue level when the floor is not short-staffed. In some embodiments, system 100 can recommend adjustments to shift schedules. In other embodiments, system 100 can be configured to override its normal functions in the event of an emergency (e.g., an all-hands-on-deck emergency where maximum alert intensity is needed to get the attention of all relevant personnel).

To the extent that it can influence an ecosystem, system 100 may likely have to compensate for a certain level of fatigue and/or risk. In other words, external factors influencing alarm fatigue levels may be present that are unaccounted in system 100. While system 100 can monitor its users to minimize those impacts, risk can likely never be reduced to zero and so system 100 can take that risk into account when determining alarm conditions.

In some embodiments, alarm management engine 300 additionally: (1) determines an alarm fatigue level delta corresponding to a difference between at least two consecutive alarm fatigue levels determined during a user's shift; (2) analyzes the status data associated with each user fatigue model update used for each of the at least two consecutive alarm fatigue levels determined during the at least one historical user's shift to determine at least one principal contributor to the at least one alarm fatigue level delta (e.g., via, for example, principal component analysis or eigenvalue decomposition it determines the causes of alarm fatigue by isolating the largest contributing factors); (3) receives an indication of a medical alert requiring a response from the first user; and (4) generates an alarm targeting the first user based on the alarm fatigue level, the at least one principal contributor, and the indication of an alert (i.e., to try to prevent alarm fatigue before it happens by addressing a particular person's own largest causes).

System 100 can exist within various operating system environments, such as cOS™. The cOS™ clinical operating system is designed to bring together clinical, financial, operational and environmental data to identify and solve complex healthcare problems such as quality, cost, and outcomes at a health system level, hospital level, service line level, physician level and the patient level. The cOS architecture is designed using principles of big data, enterprise data warehouse, and big memory that allow for proactive decision support as opposed to retrospective business intelligence. Proactive decision support allows health system executives to predict and solve problems before they occur (e.g., solve alarm fatigue problems proactively rather than retroactively). The cOS™ platform allows innovation to thrive because it is a completely open system with documented web services that can be leveraged by the health system as well as third party software development companies to build new and innovative applications.

Within the cOS™ system, system 100 can be implemented and can execute at various levels. For example, at a hospital level, system 100 can manage alarm fatigue levels of hospital personnel and staff. At a physician level, system 100 can be directed towards medical doctors currently working a shift. At a patient level, system 100 can be implemented to manage alarm fatigue levels of individuals working with a particular patient.

Some embodiments of system 100 are capable of reporting performance statistics (e.g., for JACHO) to verify that alarm fatigue levels have been reduced and that environments where system 100 has been deployed are safer than national average (e.g., system 100 has resulted in reduced overall alarm fatigue levels compared to the national average resulting in better patient care).

In various embodiments, system 100 can be applied to any type of scenario that requires attention of a user. One such application can include notifications within a computer operating system. The system could monitor user responses and determine when an alarm should be altered to better capture the attention of a user experiencing alarm fatigue. For example, scheduling software can provide notifications to remind a user of important meetings, but each of those notifications is identical and when a user has a very busy schedule that user may become desensitized to the alerts. The alarm management system can be advantageously applied to such a system to help the user from missing important meetings or deadlines.

In addition to offices and hospitals, system 100 can also be implemented in fire stations, police stations, and/or military bases, industrial settings, gaming environments, or in other industries where alarms and alerts are used heavily. For example, in a fire station, fire fighters may be subjected to many alarms per day or per shift, which could lead to alarm fatigue if nothing is done to prevent the condition from developing. The same holds true for police stations. A consequence of alarm fatigue in these situations may be delayed response times to an emergency such as a fire or a burglary. On military bases, soldiers are exposed to many different alarms that provide different types of information. Developing alarm fatigue in this setting can lead to missed alarms, and in a scenario where, for example, an alarm is sounded in a war-zone, missing that alarm can mean the difference between life and death. In industrial settings, equipment and other alarms blaring over the course of a day can result in decreased concentration of workers on their respective tasks at hand. In the operation of heavy machinery, performing tasks requiring high levels of precision, and/or handling of dangerous materials, a lapse in concentration can lead to an accident causing injuries, deaths, damage to equipment, and loss of progress. In gaming settings, an ability to perform at a high level and an immersion in the game can both be critical to a player's enjoyment of the game, which can be disrupted by an excess of warnings and/or alarms.

It should be apparent to those skilled in the art that many more modifications besides those already described are possible without departing from the inventive concepts disclosed herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The foregoing discussion provides many example embodiments of systems and methods for alarm fatigue management. Although each embodiment represents a single combination of various elements, all possible combinations of the disclosed elements are intended to be included in the broad scope of the disclosure. Thus if one embodiment comprises elements A, B, and C, and a second embodiment comprises elements B and D, then the scope of the disclosure is considered to include other remaining combinations of A, B, C, or D, even if not explicitly disclosed.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary. Note that any recitation of ranges of values herein is merely intended to serve as a shorthand method of referring individually to each separate value falling within the range. Unless otherwise indicated herein, each individual value is incorporated into the specification as if it were individually recited herein.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Note that in this Specification, references to various features (e.g., elements, structures, modules, components, steps, operations, characteristics, etc.) included in "one embodiment", "example embodiment", "an embodiment", "another embodiment", "some embodiments", "various embodiments", "other embodiments", "alternative embodiment", and the like are intended to mean that any such features are included in one or more embodiments of the present disclosure, but may or may not necessarily be combined in the same embodiments. The use of any and all examples, or exemplary language (e.g. "such as") provided with respect to certain embodiments herein is intended merely to better illuminate the invention and does not pose a limitation on the scope of the embodiments otherwise claimed. No language in the specification should be construed as indicating any non-claimed essential.

In example implementations, at least some portions of the activities outlined herein may be implemented in software in, for example, alarm management engine 12. In some embodiments, one or more of these features may be implemented in hardware, provided external to these elements, or consolidated in any appropriate manner to achieve the intended functionality. The various network elements may include software (or reciprocating software) that can coordinate in order to achieve the operations as outlined herein. In still other embodiments, these elements may include any suitable algorithms, hardware, software, components, modules, interfaces, or objects that facilitate the operations thereof.

Furthermore, alarm management engine 12 and various other components described and shown herein (and/or its associated structures) may also include suitable interfaces for receiving, transmitting, and/or otherwise communicating data or information in a network environment. Additionally, some of the processors and memory elements associated with the various nodes may be removed, or otherwise consolidated such that a single processor and a single memory element are responsible for certain activities. In a general sense, the arrangements depicted in the FIGURES may be more logical in their representations, whereas a physical architecture may include various permutations, combinations, and/or hybrids of these elements. It is imperative to note that countless possible design configurations can be used to achieve the operational objectives outlined here. Accordingly, the associated infrastructure has a myriad of substitute arrangements, design choices, device possibilities, hardware configurations, software implementations, equipment options, etc. Moreover, all methods described herein can be performed in any suitable order unless otherwise indicated herein or otherwise clearly contradicted by context.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

In some of example embodiments, one or more memory elements (e.g., memory element 38, 68) can store data used for the operations described herein. This includes the memory element being able to store instructions (e.g., software, logic, code, etc.) in non-transitory media such that the instructions are executed to carry out the activities described in this Specification. These devices may further keep information in any suitable type of non-transitory storage medium (e.g., random access memory (RAM), read only memory (ROM), field programmable gate array (FPGA), erasable programmable read only memory (EPROM), EEPROM, etc., software, hardware, or in any other suitable component, device, element, or object where appropriate and based on particular needs.

A processor can execute any type of instructions associated with the data to achieve the operations detailed herein in this Specification. In one example, processors (e.g., processor 36, 66) could transform an element or an article (e.g., data) from one state or thing to another state or thing. In another example, the activities outlined herein may be implemented with fixed logic or programmable logic (e.g., software/computer instructions executed by a processor) and the elements identified herein could be some type of a programmable processor, programmable digital logic (e.g., a field programmable gate array (FPGA), an erasable programmable read only memory (EPROM), an electrically erasable programmable read only memory (EEPROM)), an ASIC that includes digital logic, software, code, electronic instructions, flash memory, optical disks, CD-ROMs, DVD ROMs, magnetic or optical cards, other types of machine-readable mediums suitable for storing electronic instructions, or any suitable combination thereof.

The information being tracked, sent, received, or stored in system 10 could be provided in any database, register, table, cache, queue, control list, or storage structure, based on particular needs and implementations, all of which could be referenced in any suitable timeframe. Any of the memory items discussed herein should be construed as being encompassed within the broad term 'memory element.' Similarly, any of the potential processing elements, modules, and machines described in this Specification should be construed as being encompassed within the broad term 'processor.'

It is also important to note that the operations and steps described with reference to the preceding FIGURES illustrate only some of the possible scenarios that may be executed by, or within, the system. Some of these operations may be deleted or removed where appropriate, or these steps may be modified or changed considerably without departing from the scope of the discussed concepts. In addition, the timing of these operations may be altered considerably and still achieve the results taught in this disclosure. The preceding operational flows have been offered for purposes of example and discussion. Substantial flexibility is provided by the system in that any suitable arrangements, chronologies, configurations, and timing mechanisms may be provided without departing from the teachings of the discussed concepts.

Note also that the disclosed subject matter herein enables construction or configuration of a medical device to operate on digital data (e.g., raw sensor data, alarm condition, etc.), beyond the capabilities of a human or un-configured (e.g., off-the-shelf) medical device. Although the digital data represents alarm conditions, it should be appreciated that the digital data is a representation of one or more digital models of alarm conditions and not the actual alarms themselves, which comprise activities or operations performed by the medical device and/or adapters. By instantiation of such digital models in the memory of the medical device (and/or adapter), the medical device (and/or adapter) is able to manage the digital models in a manner that could provide utility to an individual (e.g., a user of the system) that the individual would lack without such a tool.

It should also be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, random access memory (RAM), flash memory, read-only memory (ROM), etc.). The software instructions can configure a suitable computing device to provide the roles, responsibilities, or other functionality as discussed herein with respect to the disclosed apparatus. In some embodiments, the various servers, systems, databases, or interfaces exchange data using standardized protocols or algorithms, possibly based on hyper-text transfer protocol (HTTP), hyper-text transfer protocol secure (HTTPS), Advanced Encryption Standard (AES), public-private key exchanges, web service application programming interfaces (APIs), known financial transaction protocols, or other electronic information exchanging methods. Data exchanges preferably are conducted over a packet-switched network, the Internet, local area network (LAN), wide area network (WAN), virtual private network (VPN), or other type of packet switched network.

As used in the description herein and throughout the claims that follow, when a system, engine, server, device, module, or other computing element is described as configured to perform or execute functions on data in a memory, the meaning of "configured to" or "programmed to" refers to one or more processors or cores of the computing element being programmed by a set of software instructions stored in the memory of the computing element to execute the set of functions on target data or data objects stored in the memory.

One should appreciate that the disclosed techniques provide many advantageous technical effects including reduction in latency between a computing device ingesting healthcare data and generating a prediction or recommendation. Latency is reduced through storage of health care data in a memory and in the form of N-grams, which can be computationally analyzed quickly.

Although the present disclosure has been described in detail with reference to particular arrangements and configurations, these example configurations and arrangements may be changed significantly without departing from the scope of the present disclosure. For example, although the present disclosure has been described with reference to particular communication exchanges involving certain network access and protocols, system 10 may be applicable to other exchanges or routing protocols. Moreover, although system 10 has been illustrated with reference to particular elements and operations that facilitate the communication process, these elements, and operations may be replaced by any suitable architecture or process that achieves the intended functionality of system 10.

Numerous other changes, substitutions, variations, alterations, and modifications may be ascertained to one skilled in the art and it is intended that the present disclosure encompass all such changes, substitutions, variations, alterations, and modifications as falling within the scope of the appended claims. In order to assist the United States Patent and Trademark Office (USPTO) and, additionally, any readers of any patent issued on this application in interpreting the claims appended hereto, Applicant wishes to note that the Applicant: (a) does not intend any of the appended claims to invoke paragraph six (6) or (f) of 35 U.S.C. section 112 as it exists on the date of the filing hereof unless the words "means for" or "step for" are specifically used in the particular claims; and (b) does not intend, by any statement in the specification, to limit this disclosure in any way that is not otherwise reflected in the appended claims.

What is claimed is:

1. A computing device comprising:
one or more hardware processors configured to execute program instructions to cause the computing device to:
monitor user data corresponding to real-time user activities of a user;
update an alarm fatigue level of the user in real-time based on at least the user data, the alarm fatigue level corresponding to a likelihood the user responds to notifications;
before generating a first notification of a computer operating system, set an attribute of the first notification of the computer operating system based on at least the alarm fatigue level of the user, wherein the attribute is configured to increase the likelihood the user responds to the first notification to proactively reduce the likelihood of alarm fatigue and a need for a second notification before the alarm fatigue occurs, wherein setting the attribute of the first notification comprises setting one or more of a notification intensity or a notification duration to differentiate the first notification from other notifications to which the user has responded; and
generate the first notification with the attribute.

2. The computing device of claim 1, wherein the computing device comprises a personal alarm device.

3. The computing device of claim 1, wherein the computing device comprises a watch.

4. The computing device of claim 1, wherein the one or more hardware processors is further configured to execute the program instructions to cause the computing device to generate the first notification on a personal alarm device, the personal alarm device comprising a watch.

5. The computing device of claim 1, wherein the user data corresponding to the real-time user activities comprises user responses to alerts or notifications.

6. The computing device of claim 1, wherein the user data corresponding to the real-time user activities comprises physiological data of the user, the physiological data comprising one or more physiological parameters relating to a physiological status of the user.

7. The computing device of claim 1, wherein the one or more hardware processors is further configured to execute the program instructions to cause the computing device to set the attribute of the first notification by setting a notification distribution mode from one mode to another mode including one or more of a visual mode, an auditory mode, or a tactile mode, wherein the notification intensity comprises one or more of a light intensity or an audio intensity based on the notification distribution mode.

8. The computing device of claim 1, wherein the one or more hardware processors is further configured to execute the program instructions to cause the computing device to set the attribute of the first notification by setting one or more of a notification frequency or a notification threshold.

9. The computing device of claim 1, wherein the one or more hardware processors is further configured to execute the program instructions to cause the computing device to set the attribute of the first notification based on at least a subscription level corresponding to a subscription service.

10. The computing device of claim 1, wherein the one or more hardware processors is further configured to execute the program instructions to cause the computing device to set the attribute of the first notification based on at least a subscription level, the subscription level based on at least a location of the computing device or the user.

11. The computing device of claim 1, wherein the one or more hardware processors is further configured to execute the program instructions to cause the computing device to set the attribute of the first notification by deleting the first notification.

12. A computer-implemented method comprising:
by one or more computer processors executing program instructions:
monitoring user data corresponding to real-time user activities of a user;
updating an alarm fatigue level of the user in real-time based on at least the user data, the alarm fatigue level corresponding to a likelihood the user responds to notification;
before generating a first notification of a computer operating system, setting an attribute of the first notification of the computer operating system based on at least the alarm fatigue level of the user, wherein the attribute is configured to increase the likelihood the user responds to the first notification to proactively reduce the likelihood of alarm fatigue and a need for a second notification before the alarm fatigue occurs, wherein setting the attribute of the first notification comprises setting one or more of a notification intensity or a notification duration to differentiate the first notification from other notifications to which the user has responded; and
generating the first notification with the attribute.

13. The computer-implemented method of claim 12, further comprising generating the first notification on a personal alarm device, the personal alarm device comprising a watch.

14. The computer-implemented method of claim 12, wherein the user data corresponding to the real-time user activities comprises physiological data of the user, the physiological data comprising one or more physiological parameters relating to a physiological status of the user.

15. The computer-implemented method of claim 12, further comprising setting the attribute of the first notification by setting a notification distribution mode from one mode to another mode including one or more of a visual mode, an auditory mode, or a tactile mode, wherein the notification intensity comprises one or more of a light intensity or an audio intensity based on the notification distribution mode.

16. The computer-implemented method of claim 12, further comprising setting the attribute of the first notification by setting one or more of a notification frequency or a notification threshold.

17. The computer-implemented method of claim 12, further comprising setting the attribute of the first notification based on at least a subscription level corresponding to a subscription service.

18. Non-transitory computer-readable media including computer-executable instructions that, when executed by a computing system, cause the computing system to perform operations comprising:
monitoring user data corresponding to real-time user activities of a user;
updating an alarm fatigue level of the user in real-time based on at least the user data, the alarm fatigue level corresponding to a likelihood the user responds to notifications;
before generating a first notification of a computer operating system, setting an attribute of the first notification of the computer operating system based on at least the alarm fatigue level of the user, wherein the attribute is configured to increase the likelihood the user responds to the first notification to proactively reduce the likelihood of alarm fatigue and a need for a second notification before the alarm fatigue occurs, wherein setting the attribute of the first notification comprises setting one or more of a notification intensity or a notification duration to differentiate the first notification from other notifications to which the user has responded; and
generating the first notification with the attribute.

19. The non-transitory computer-readable media of claim 18, wherein the computer-executable instructions, when executed by the computing system, further cause the computing system to perform operations comprising generating the first notification on a personal alarm device, the personal alarm device comprising a watch.

20. The non-transitory computer-readable media of claim 18, wherein the user data corresponding to the real-time user activities comprises physiological data of the user, the physiological data comprising one or more physiological parameters relating to a physiological status of the user.

* * * * *